US011744235B2

(12) United States Patent
Sobecki et al.

(10) Patent No.: US 11,744,235 B2
(45) Date of Patent: Sep. 5, 2023

(54) SIEVING APPARATUSES FOR PUPAE SEPARATION

(71) Applicant: Verily Life Sciences LLC, South San Francisco, CA (US)

(72) Inventors: Robert Sobecki, Brisbane, CA (US); Charles Behling, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 18/070,264

(22) Filed: Nov. 28, 2022

(65) Prior Publication Data

US 2023/0107016 A1 Apr. 6, 2023

Related U.S. Application Data

(60) Continuation of application No. 16/947,315, filed on Jul. 28, 2020, now Pat. No. 11,517,001, which is a
(Continued)

(51) Int. Cl.
*A01K 67/033* (2006.01)
*B08B 3/04* (2006.01)
(Continued)

(52) U.S. Cl.
CPC ............. *A01K 67/033* (2013.01); *B07B 1/28* (2013.01); *B07B 1/46* (2013.01); *B07B 1/469* (2013.01);
(Continued)

(58) Field of Classification Search
CPC .......... A01K 67/033; B07B 1/28; B07B 1/46; B07B 1/469; B07B 1/55; B08B 3/045; B08B 3/047
See application file for complete search history.

(56) References Cited

U.S. PATENT DOCUMENTS 271,497 A 1/1883 McClure
575,095 A 1/1897 Bartelt
(Continued)

FOREIGN PATENT DOCUMENTS

CN 202070486 U 12/2011
CN 202310909 U 7/2012
(Continued)

OTHER PUBLICATIONS

"First Research Co-Origination Meeting", Joint FAO/IAEA Division of Nuclear Techniques in Food and Agriculture, Co-Ordinated Research Programme on Explore Mechanical, Molecular, Behavioural or Genetic Methods of Sex Separation in Mosquitoes, Sep. 30-Oct. 4, 2013, 53 pages.
(Continued)

*Primary Examiner* — Terrell H Matthews
(74) *Attorney, Agent, or Firm* — Kilpatrick Townsend & Stockton LLP

(57) ABSTRACT

A male population of mosquito pupae sorted according to a sorting method is described. The sorting method may include adding a mixed population of mosquito pupae into an interior volume of a sieving container including base defining a set of openings enabling movement of mosquito pupae from the interior volume through the set of openings. The mixed population of mosquito pupae may include male mosquito pupae and female mosquito pupae. The method may also include adding a volume of aqueous solution to the interior volume. The method may also include removing a portion of the male pupae from the mixed population of mosquito pupae to by performing a sieving action that causes the portion of the male pupae and a portion of the volume of water to pass from the interior volume through the set of openings. The method may also include capturing the portion of the male pupae as the male population of mos-
(Continued)

quito pupae after the portion of the male pupae has passed through the set of openings.

20 Claims, 11 Drawing Sheets

Related U.S. Application Data division of application No. 16/154,656, filed on Oct. 8, 2018, now Pat. No. 10,772,309, which is a continuation-in-part of application No. 15/945,851, filed on Apr. 5, 2018, now Pat. No. 10,251,380, which is a division of application No. 15/467,152, filed on Mar. 23, 2017, now Pat. No. 9,992,983.

(51) Int. Cl.
  *B07B 1/46* (2006.01)
  *B07B 1/28* (2006.01)
  *B07B 1/55* (2006.01)

(52) U.S. Cl.
  CPC ............... *B07B 1/55* (2013.01); *B08B 3/045* (2013.01); *B08B 3/047* (2013.01); *B07B 2230/01* (2013.01)

(56) References Cited

U.S. PATENT DOCUMENTS

| | | |
|---|---|---|
| 1,468,261 A | 9/1923 | Collins |
| 1,595,685 A | 8/1926 | Parini |
| 1,886,174 A | 11/1932 | Flint et al. |
| 1,989,005 A | 1/1935 | Fink et al. |
| 2,135,069 A | 11/1938 | Deister et al. |
| 2,449,666 A | 9/1948 | Moseley |
| 2,520,718 A | 8/1950 | Hanson |
| 2,861,688 A | 11/1958 | Harms |
| 3,194,397 A | 7/1965 | Taege |
| 3,223,237 A | 12/1965 | Harrod, Jr. et al. |
| 3,334,750 A | 8/1967 | Ullman, Jr. |
| 3,363,769 A | 1/1968 | Wilmot et al. |
| 3,696,788 A | 10/1972 | Day et al. |
| 3,997,999 A | 12/1976 | Evans |
| 4,137,353 A | 1/1979 | Fariello |
| 4,328,636 A | 5/1982 | Johnson |
| 4,473,466 A | 9/1984 | Schmidt et al. |
| 4,903,636 A | 2/1990 | Kroeker |
| 5,108,588 A | 4/1992 | Yu |
| 5,221,008 A | 6/1993 | Derrick, Jr. et al. |
| 5,665,207 A | 9/1997 | Aikawa |
| 5,873,327 A | 2/1999 | Holyoak |
| 6,474,259 B1 | 11/2002 | Gaugler |
| 6,676,051 B2 | 1/2004 | Rebordosa et al. |
| 6,708,443 B2 | 3/2004 | Hall |
| 6,990,768 B1 | 1/2006 | Boston |
| 7,810,649 B2 | 10/2010 | Robertson |
| 7,861,866 B1 | 1/2011 | Ondrias |
| 7,867,396 B2 | 1/2011 | Hill |
| 8,025,027 B1 | 9/2011 | Morales-Ramos et al. |
| 8,109,035 B2 | 2/2012 | Bowden et al. |
| 8,123,912 B2 | 2/2012 | Gindele et al. |
| 8,517,180 B2 | 8/2013 | Raichle et al. |
| 8,844,465 B2 | 9/2014 | Holland et al. |
| 9,010,539 B2 | 4/2015 | Lipa et al. |
| 9,180,464 B2 | 11/2015 | Nimmo et al. |
| 9,265,247 B2 | 2/2016 | Gaugler et al. |
| 9,855,518 B2 | 1/2018 | Wright et al. |
| 9,884,344 B2 | 2/2018 | Wojciechowski |
| 9,992,983 B1 * | 6/2018 | Sobecki ............... A01K 67/033 |
| 10,251,380 B2 | 4/2019 | Sobecki et al. |
| 10,259,012 B2 | 4/2019 | Robertson et al. |
| 10,342,222 B2 | 7/2019 | Sobecki et al. |
| 10,450,238 B2 | 10/2019 | Caesar |
| 10,499,620 B2 | 12/2019 | Sobecki et al. |
| 10,835,925 B2 | 11/2020 | Sobecki et al. |
| 10,842,137 B2 | 11/2020 | Sobecki et al. |
| 10,926,295 B1 * | 2/2021 | Greeley ............... A01K 67/033 |
| 2002/0184982 A1 | 12/2002 | Smith et al. |
| 2004/0206671 A1 | 10/2004 | Stichert |
| 2010/0018910 A1 | 1/2010 | Ballman |
| 2013/0277282 A1 | 10/2013 | Lipa et al. |
| 2014/0166307 A1 | 6/2014 | Cady |
| 2015/0008163 A1 * | 1/2015 | Nimmo ................. B07B 1/4636 209/676 |
| 2015/0183658 A1 | 7/2015 | Wright et al. |
| 2017/0042131 A1 | 2/2017 | Unger |
| 2018/0077912 A1 | 3/2018 | Comparat et al. |
| 2018/0236491 A1 | 8/2018 | Gold |
| 2018/0271072 A1 | 9/2018 | Sobecki et al. |
| 2018/0271073 A1 | 9/2018 | Sobecki et al. |
| 2018/0271074 A1 | 9/2018 | Sobecki et al. |
| 2018/0369867 A1 | 12/2018 | Sobecki et al. |
| 2019/0037819 A1 * | 2/2019 | Sobecki .................... B07B 1/55 |
| 2019/0166811 A1 | 6/2019 | Sobecki et al. |
| 2021/0346913 A1 | 11/2021 | Greeley et al. |
| 2022/0053743 A1 | 2/2022 | Lepek et al. |

FOREIGN PATENT DOCUMENTS

| | | |
|---|---|---|
| CN | 103704179 A | 4/2014 |
| CN | 203646342 U | 6/2014 |
| CN | 203692226 U | 7/2014 |
| CN | 204232011 U | 4/2015 |
| CN | 204232124 U | 4/2015 |
| CN | 207721014 U * | 8/2018 |
| CN | 108620306 A | 10/2018 |
| CN | 108620313 A | 10/2018 |
| CN | 208824934 U | 5/2019 |
| CN | 208853213 U | 5/2019 |
| KR | 101372332 B1 | 3/2014 |
| SG | 10201802345X A | 10/2018 |
| SG | 10201802413Y A | 10/2018 |
| SG | 10201903101R A | 5/2019 |
| SG | 10201802345X | 1/2020 |
| WO | 03007710 A1 | 1/2003 |
| WO | WO-2013140167 A1 * | 9/2013 ........... A01K 67/033 |
| WO | 2016024164 A1 | 2/2016 |
| WO | 2018175207 A1 | 9/2018 |
| WO | 2018175209 A1 | 9/2018 |
| WO | WO-2018175209 A1 * | 9/2018 ........... A01K 67/033 |

OTHER PUBLICATIONS

U.S. Appl. No. 15/467,145 , "Corrected Notice of Allowability", dated May 22, 2019, 3 pages.
U.S. Appl. No. 15/467,145 , Non-Final Office Action, dated Jun. 25, 2018, 13 pages.
U.S. Appl. No. 15/467,145 , Notice of Allowance, dated Feb. 13, 2019, 6 pages.
U.S. Appl. No. 15/467,145 , "Restriction Requirement", dated Apr. 11, 2018, 6 pages.
U.S. Appl. No. 15/467,152 , Notice of Allowance, dated Mar. 29, 2018, 11 pages.
U.S. Appl. No. 15/467,152 , "Restriction Requirement", dated Dec. 14, 2017, 6 pages.
U.S. Appl. No. 15/467,152 , "Supplemental Notice of Allowability", dated Apr. 16, 2018, 3 pages.
U.S. Appl. No. 15/945,851 , Notice of Allowance, dated Nov. 27, 2018, 12 pages.
U.S. Appl. No. 15/945,851 , Notice of Allowance, dated Sep. 12, 2018, 14 pages.
U.S. Appl. No. 15/945,851 , "Supplemental Notice of Allowability", dated Dec. 20, 2018, 2 pages.
U.S. Appl. No. 15/990,461 , "Corrected Notice of Allowability", dated Aug. 31, 2020, 2 pages.
U.S. Appl. No. 15/990,461 , "Corrected Notice of Allowability", dated Sep. 22, 2020, 2 pages.
U.S. Appl. No. 15/990,461 , Final Office Action, dated Nov. 6, 2019, 13 Pages.

(56) References Cited

OTHER PUBLICATIONS

U.S. Appl. No. 15/990,461, Non-Final Office Action, dated Mar. 23, 2020, 13 pages.
U.S. Appl. No. 15/990,461, Non-Final Office Action, dated May 3, 2019, 13 pages.
U.S. Appl. No. 15/990,461, Notice of Allowance, dated Jul. 20, 2020, 5 pages.
U.S. Appl. No. 16/117,758, "Corrected Notice of Allowability", dated Aug. 31, 2020, 2 pages.
U.S. Appl. No. 16/117,758, "Corrected Notice of Allowability", dated Sep. 22, 2020, 2 pages.
U.S. Appl. No. 16/117,758, Non-Final Office Action, dated Mar. 25, 2020, 13 pages.
U.S. Appl. No. 16/117,758, Notice of Allowance, dated Jul. 20, 2020, 8 pages.
U.S. Appl. No. 16/154,656, "Corrected Notice of Allowability", dated Apr. 24, 2020, 2 pages.
U.S. Appl. No. 16/154,656, "Notice of Allowability", dated Jul. 9, 2020, 3 pages.
U.S. Appl. No. 16/154,656, Notice of Allowance, dated Apr. 8, 2020, 11 pages.
U.S. Appl. No. 16/269,451, "Corrected Notice of Allowability", dated Sep. 10, 2019, 2 pages.
U.S. Appl. No. 16/269,451, "Corrected Notice of Allowability", dated Nov. 1, 2019, 3 pages.
U.S. Appl. No. 16/269,451, Notice of Allowance, dated Aug. 5, 2019, 10 pages.
U.S. Appl. No. 16/947,315, Non-Final Office Action, dated Jan. 12, 2022, 6 pages.
U.S. Appl. No. 16/947,315, Notice of Allowance, dated Aug. 10, 2022, 10 pages.
U.S. Appl. No. 16/949,692, Non-Final Office Action, dated Apr. 21, 2022, 11 pages.
Bellini et al., "Use of the Sterile Insect Technique Against Aedes Albopictus in Italy: First Results of a Pilot Trial", Area-wide Control of Insect Pests, Springer Netherlands, Jan. 2007, pp. 1-11.
Application No. CN201810241159.0, Notice of Decision to Grant, dated Jun. 10, 2020, 5 pages.
Application No. CN201810241159.0, Office Action, dated Jan. 22, 2020, 12 pages.
Application No. CN201810241159.0, Office Action, dated Jul. 24, 2019, 12 pages.
Application No. CN201810243591.3, Notice of Decision to Grant, dated Apr. 26, 2022, 7 pages.
Application No. CN201810243591.3, Office Action, dated Aug. 19, 2020, 12 pages.
Application No. CN201810243591.3, Office Action, dated Jun. 7, 2021, 27 pages.
Application No. CN201810243591.3, Office Action, dated Nov. 2, 2021, 4 pages.
Application No. CN201820397471.4, Notice of Decision to Grant, dated Feb. 12, 2019, 2 pages.
Application No. CN201820397471.4, Office Action, dated Nov. 6, 2018, 4 pages.
Application No. CN201820400218.X, Notice of Decision to Grant, dated Mar. 1, 2019, 2 pages.
Application No. CN201820400218.X, Office Action, dated Nov. 21, 2018, 3 pages.
Application No. CN202010863017.5, Office Action, dated Oct. 19, 2022, 4 pages.
Application No. CN202010863017.5, Office Action, dated Mar. 30, 2022, 6 pages.
Endecotts, "Test Sieves—All Signed and International Standards—Endecotts", Available Online at: http://www.endecotts.com/products/sieves, Jan. 17, 2017, 12 pages.
Hock, "Improved Separator for the Developmental Stages, Sexes, and Species of Mosquitoes", Available online at: http://johnwhock.com/products/laboratoryequipment/larvalpupal-separator/, Model 5412 Instructions, vol. 17, No. 6, Dec. 30, 1980, 1 page.
Mikery-Pacheco et al., "Efficiency of the Separation of Aedes (Stegomyia) Albopictus (Diptera: Culicidae) Male and Female Pupae Using a Sieving Device", Acta Zoológica Mexicana 31.1, vol. 31, No. 1, Apr. 2015, pp. 113-115.
Application No. PCT/US2018/022687, International Preliminary Report on Patentability, dated Oct. 3, 2019, 11 pages.
Application No. PCT/US2018/022687, International Search Report and Written Opinion, dated Jul. 26, 2018, 14 pages.
PCT/US2018/022687, "Invitation to Pay Additional Fees and Partial Search Report", dated May 31, 2018, 2 pages.
Application No. PCT/US2018/022690, International Preliminary Report on Patentability, dated Oct. 3, 2019, 12 pages.
Application No. PCT/US2018/022690, International Search Report and Written Opinion, dated Aug. 1, 2018, 15 pages.
PCT/US2018/022690, "Invitation to Pay Additional Fees and Partial Search Report", dated May 31, 2018, 2 pages.
Application No. SG10201802345X, Further Written Opinion, dated Aug. 26, 2019, 3 pages.
Application No. SG10201802345X, Notice of Decision to Grant, dated Nov. 6, 2019, 6 pages.
Application No. SG10201802345X, Written Opinion, dated Mar. 25, 2019, 8 pages.
Application No. SG10201802413Y, Notice of Decision to Grant, dated Jan. 23, 2020, 4 pages.
Application No. SG10201903101R, Notice of Decision to Grant, dated Apr. 9, 2021, 1 page.
Application No. SG10202002401P, Notice of Decision to Grant, dated Jan. 19, 2021, 8 pages.

* cited by examiner

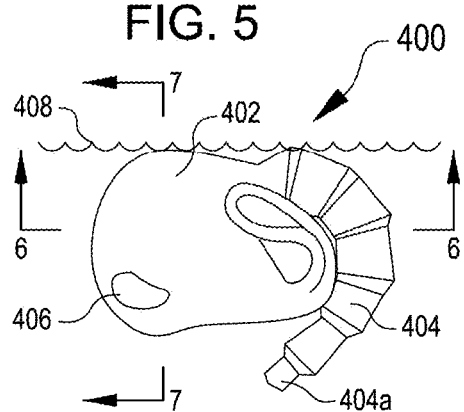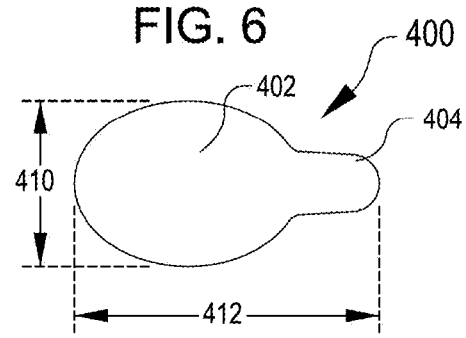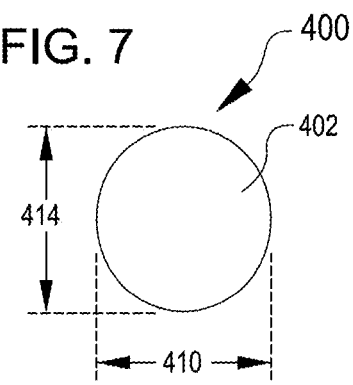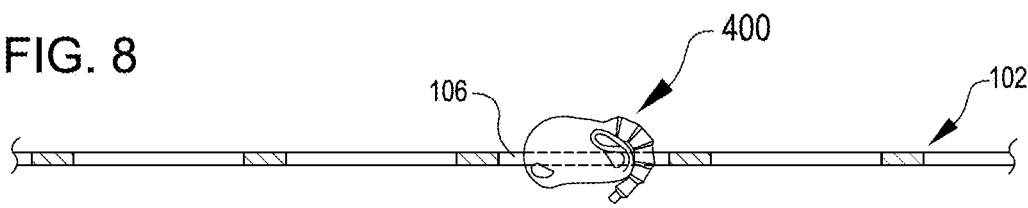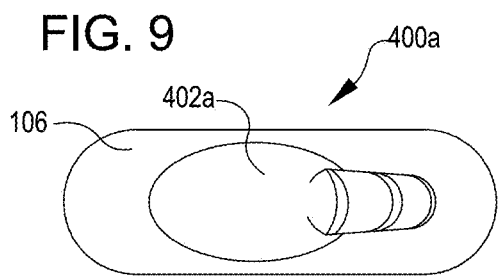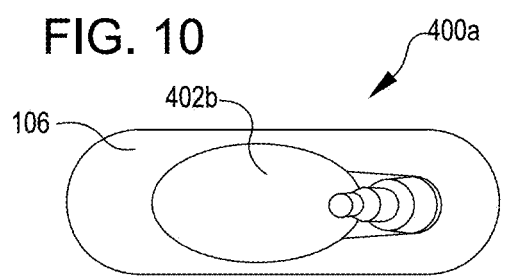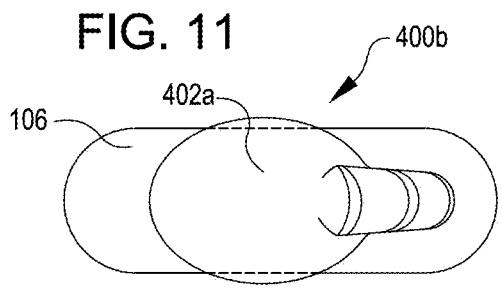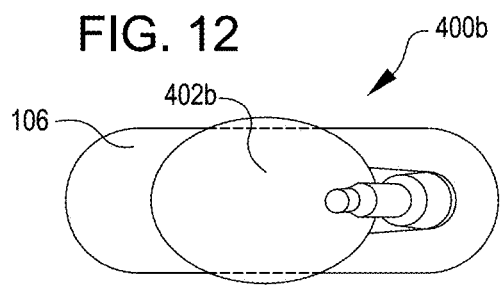

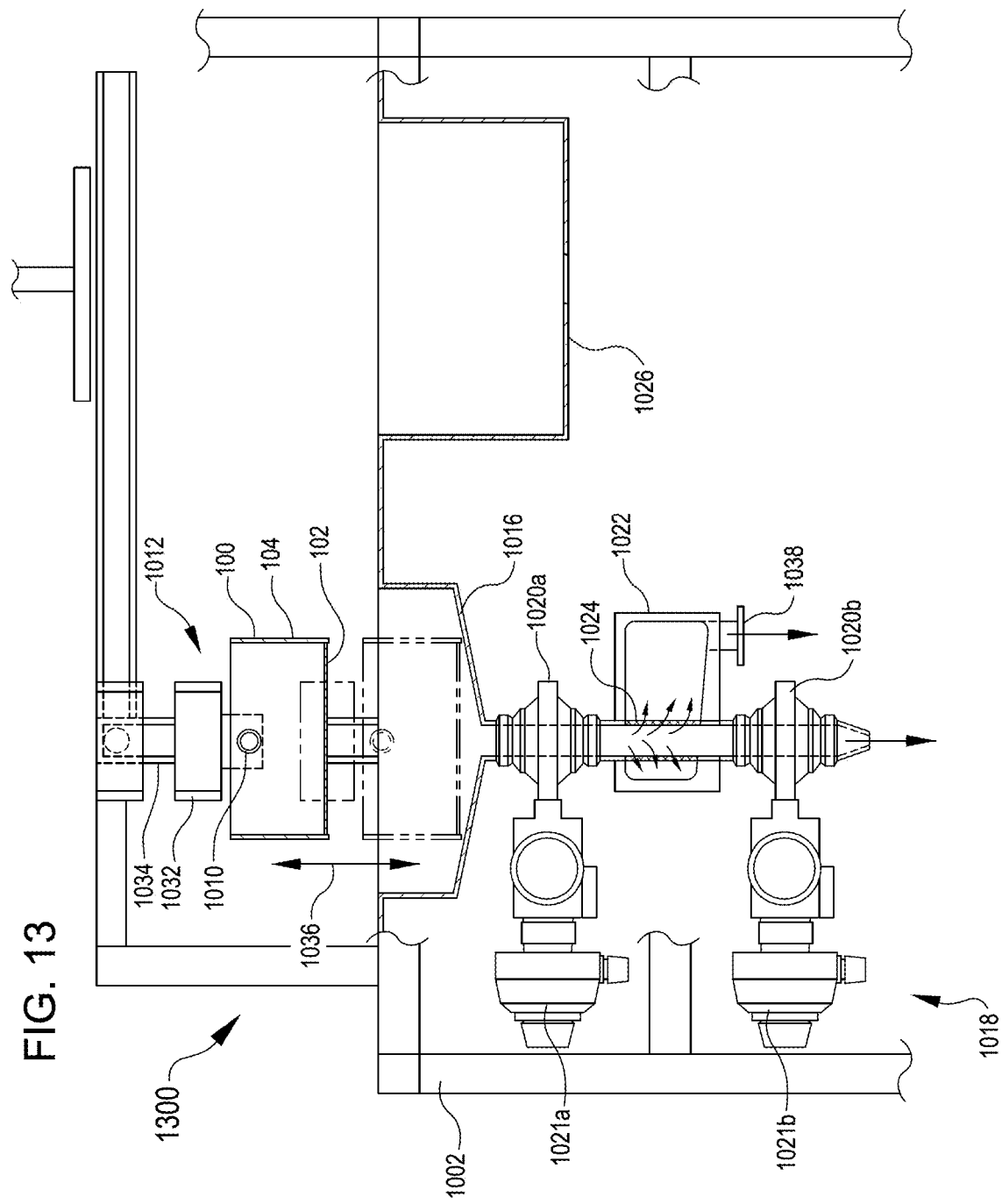

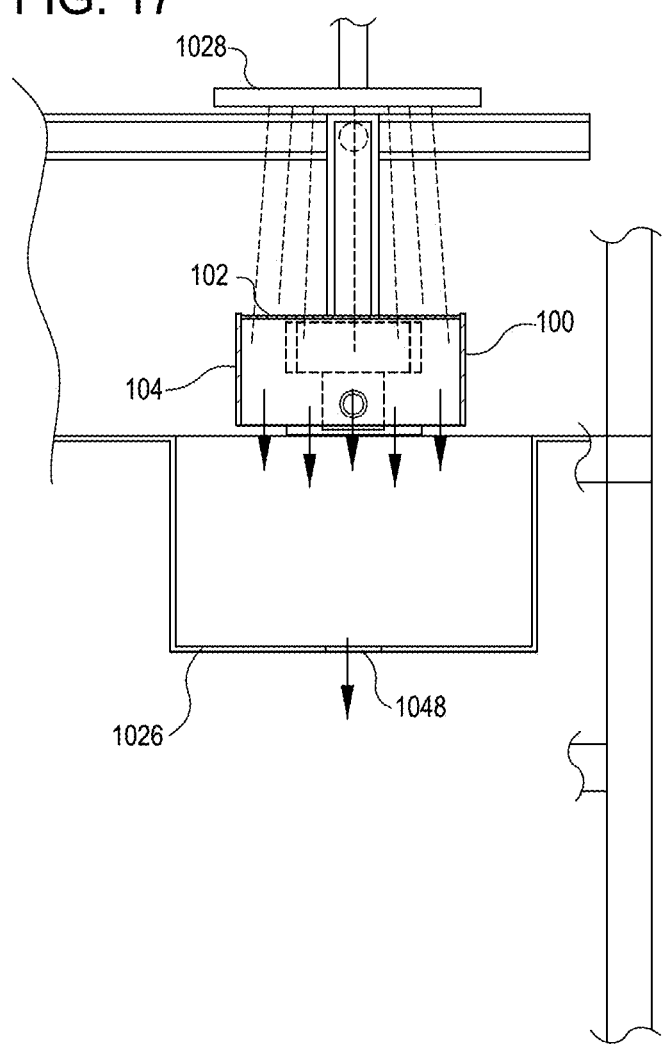

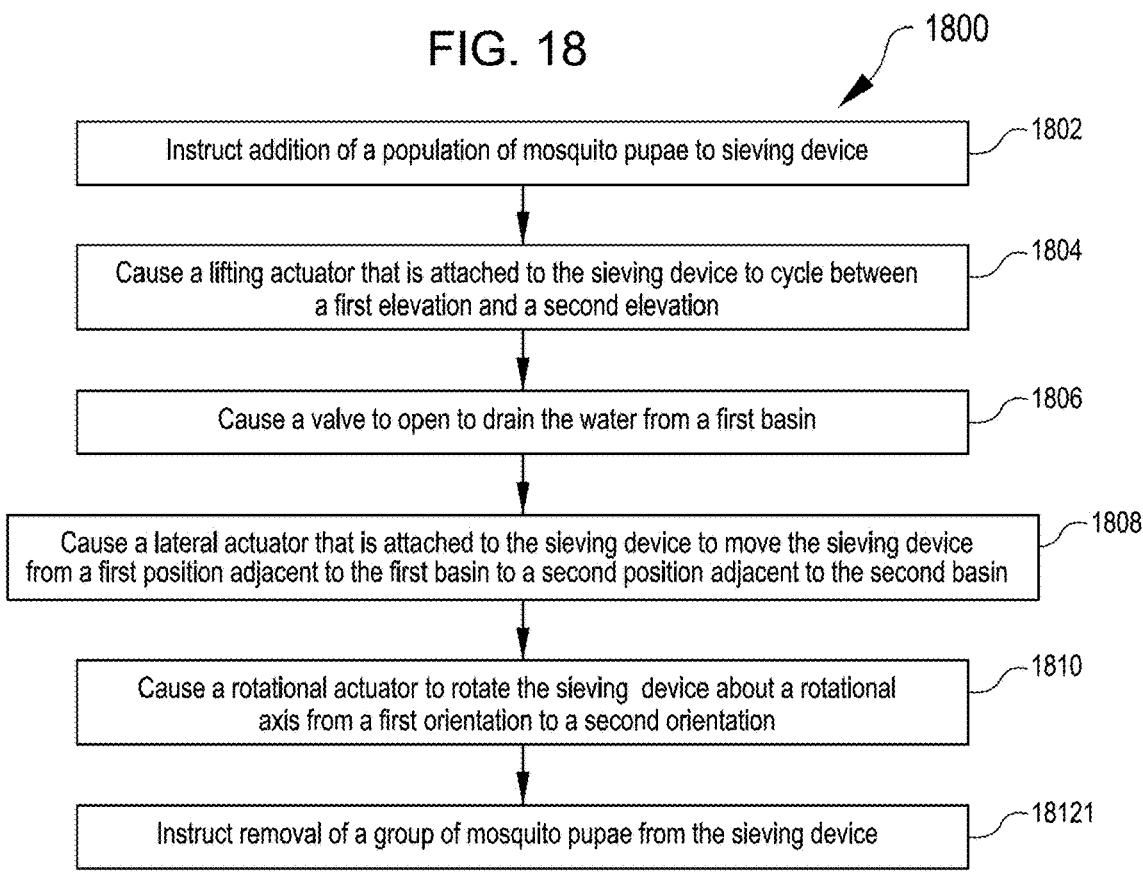
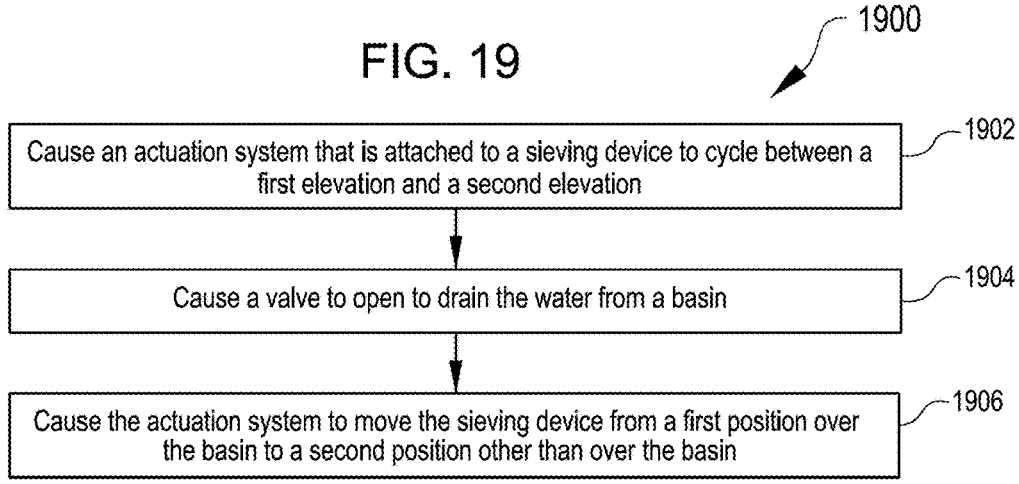
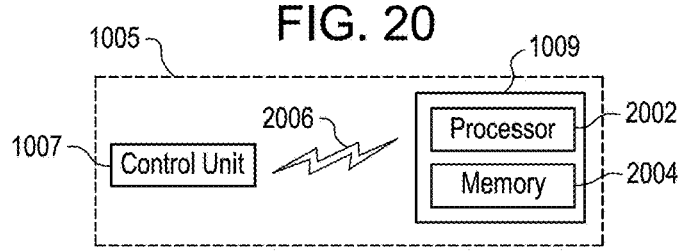

SIEVING APPARATUSES FOR PUPAE SEPARATION

CROSS REFERENCE TO RELATED APPLICATION

The present application is continuation of U.S. patent application Ser. No. 16/947,315 filed Jul. 28, 2020, which is a divisional of U.S. patent application Ser. No. 16/154,656, filed Oct. 8, 2018, now U.S. Pat. No. 10,772,309, which is a continuation-in-part of U.S. patent application Ser. No. 15/945,851, now U.S. Pat. No. 10,251,380, filed Apr. 5, 2018, which is a divisional of U.S. patent application Ser. No. 15/467,152, now U.S. Pat. No. 9,992,983, filed Mar. 23, 2017, which are incorporated by reference in their entireties herein.

BACKGROUND

Generally, a sieve can be formed of a wire or plastic mesh held in a frame. The sieve can be used for straining solids from liquid or for separating coarser objects from finer objects.

Among those objects that can be separated are insects. Other devices have been designed to separate insects such as a device that includes parallel glass plates. The reasons for separating insects are various. For example, as part of a Sterile Insect Technique (SIT) program, male insects may be separated from female insects. Depending on the program, separation may be performed at one or more stages of insect development. For example, insects having an aqueous pupal stage may be separated while in the pupal stage.

Use of conventional mesh screens to separate pupae may create challenges given the physiological structures of the pupae. Additionally, use of devices including parallel glass plates may create challenges given their difficulty to operate and required user interaction. These challenges may result in prohibitively low throughput and similarly low yield.

SUMMARY

Various examples are described relating to sieving devices, systems including the sieving devices, methods for using the sieving devices, and methods for forming the sieving devices.

In an example, an apparatus is described. The apparatus includes a frame. The apparatus also includes a sieving device including: an adjustable sieve surface including a first side and a second side, where a set of openings is formed in the adjustable sieve surface to define a set of pathways extending between the first side and the second side, individual openings of the set of openings defined by: a length dimension measured along a longitudinal axis of a respective opening and a width dimension measured along a transverse axis of the respective opening, the length dimension greater than the width dimension. The apparatus also includes a sieve rim defining an interior volume, the adjustable sieve surface is attached to the sieve rim with the first side of the adjustable sieve surface exposed to the interior volume. The apparatus also includes a basin attached to the frame and sized to receive the sieving device and to retain a liquid. The apparatus also includes an actuation system attached to the frame and the sieving device. The actuation system is configured to move the sieving device between a first position within the basin and a second position within the basin. The second position is different than the first position. Moving the sieving device between the first and second position separates a population of pupae within the liquid based on cephalothorax size.

In another example, an apparatus is described. The apparatus includes a frame. The apparatus also includes a sieving container including a base and a perimeter wall encircling the base to form an interior volume of the sieving container. The perimeter wall is fixedly coupled to the base. The base defines a set of openings that enable movement of insects through the set of openings from the interior volume of the sieving container. The apparatus also includes a basin attached to the frame. The basin is sized to receive the sieving container and to retain a liquid. The apparatus also includes an actuation system attached to the frame and the sieving container. The actuation system is configured to move the sieving container. Moving the sieving container separates a population of insects present in the interior volume based on cephalothorax width.

In another example, an apparatus is described. The apparatus includes a frame. The apparatus also includes a sieving container including a base. The base includes a first sieve surface, where a first set of openings is formed in the first sieve surface so as to define a first set of pathways extending between a first side of the first sieve surface and a second side of the first sieve surface. The base also includes a second sieve surface, where a second set of openings is formed in the second sieve surface so as to define a second set of pathways extending between a third side of the second sieve surface and a fourth side of the second sieve surface. The base also includes an alignment structure configured to connect the second side of the first sieve surface and the third side of the second sieve surface and enable movement of at least one of the first sieve surface or the second sieve surface with respect to the other sieve surface. The sieving container also includes a sieve rim including a perimeter wall encircling the base and coupled to the base, the perimeter wall defining an interior volume. The apparatus also includes an actuation system attached to the frame and the sieve rim, the actuation system configured to move the sieving container in manner that separates a population of pupae within the interior volume based on cephalothorax size.

The illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 5 illustrates a side view of an example mosquito pupa that can be separated using a sieving device as described herein, according to at least one example.

FIG. 6 illustrates a profile view of an example mosquito pupa that can be separated using a sieving device as described herein, according to at least one example.

FIG. 7 illustrates a profile view of an example mosquito pupa that can be separated using a sieving device as described herein, according to at least one example.

FIG. 8 illustrates a side view of a mosquito pupa passing through an opening of a sieve surface, according to at least one example.

FIG. 9 illustrates a mosquito pupa aligned in a first orientation with respect an opening, according to at least one example.

FIG. 10 illustrates a mosquito pupa aligned in a second orientation with respect an opening, according to at least one example.

FIG. 11 illustrates a mosquito pupa aligned in a first orientation with respect an opening, according to at least one example.

FIG. 12 illustrates a mosquito pupa aligned in a second orientation with respect an opening, according to at least one example.

FIG. 13 illustrates a detailed view of an example state of the sieving apparatus from FIG. 1, according to at least one example.

FIG. 17 illustrates a detailed view of an example state of the sieving apparatus from FIG. 1, according to at least one example.

FIG. 18 illustrates an example process for separating a population of pupae based on size, according to at least one example.

FIG. 19 illustrates an example process for separating a population of pupae based on size, according to at least one example.

FIG. 20 illustrates an example computer system, according to at least one example.

DETAILED DESCRIPTION

Figure 1:
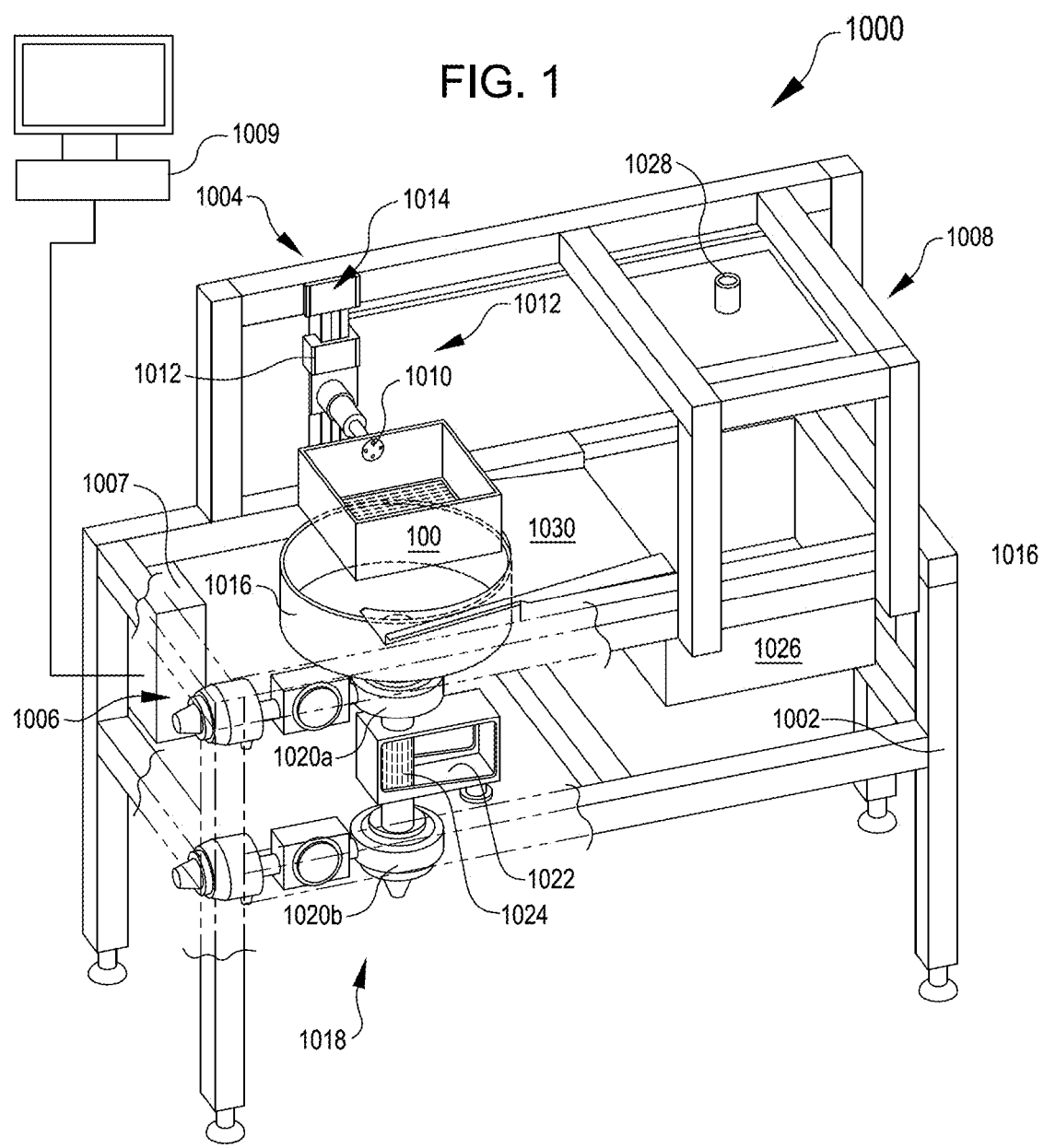
FIG. 1 illustrates a perspective view of a sieving apparatus, according to at least one example.

Examples are described herein in the context of sieving apparatuses utilizing sieving devices for use in separation of mosquito pupae. Those of ordinary skill in the art will realize that the following description is illustrative only and is not intended to be in any way limiting. For example, the sieving apparatus described herein can be used to separate any insects having an aqueous pupal stage. The sieving apparatus may be used with sieving devices having different characteristics to enable separation of other organic and inorganic materials. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a sieving apparatus for separation of pupae is described. The sieving apparatus includes a support frame and a set of components attached to the support frame. These components include a funnel basin, a rinse basin, a sieving device, a drainage system connected to the funnel basin, and an actuation system attached to the sieving device. The actuation system is configured to adjust the position and orientation of the sieving device with respect to the two basins as part of a process for separating pupae. The sieving device includes a sieve held within a rim. Together the sieve and the rim from a box-like structure, with the sieve forming the bottom of the box-like structure. The sieve includes a series of elongate openings. Each elongate opening is defined by a length corresponding to a longitudinal axis and a width corresponding to a transverse axis. A value of the width is selected to correspond to a smallest dimension of a cephalothorax of a representative pupa to be separated. For example, to separate male pupae from female pupae, a value of the width can be selected that is smaller than the cephalothoraxes of all females of a given population and larger than the cephalothoraxes of most, if not all, males of the same population. The elongate shape of the openings closely corresponds to how the pupae naturally orient in still water. When the water is flushed through the elongate openings, those pupae already in this natural orientation remain so and those that are not are oriented by the flowing water. Sizing the elongate openings to correspond to the size and natural orientation of the pupae can result in high separation rates. Additionally, high separation rates are possible because, unlike mesh sieves, the sieve surface is designed to include smooth transitions between the elongate openings. This results in fewer pupae becoming entangled, e.g., by their paddles or other physiological structures, with the openings.

To begin the separation process, water is added to the funnel basin and the actuation system is instructed to lower the sieving device into the water. The population including males and females are added to the water that is within the rim of the sieving device (e.g., within the box-like structure). The actuation system is instructed to vertically lower and raise the sieving device into and out of the water to draw the pupae down on to the sieve. In some examples, the water level is raised and lowered relative to the sieving device. Water can be flushed through the sieving device (e.g., by adjusting an elevation of the water relative to the sieve or adjusting an elevation of the sieve relative to the water). Such flushing may be repeated, such as by oscillating or agitating movement of the sieving device or the water elevation, to perform a sieving action. Using this flushing action, most of the male pupae can pass through any one of the elongate openings, while the female pupae are prevented from passing because of their larger cephalothoraxes. Such flushing may be repeated, such as by oscillating or agitating movement of the sieve device or the water elevation, to perform a sieving action. Because the sieve rim is never fully submerged during the dunking, most female pupae remain within the rim and most male pupae move into the water outside the rim. After flushing, the actuation system is instructed to move the sieving device toward the rinse basin. At the rinse basin, the sieving device is rotated and the female pupae are flushed from the sieving device. Meanwhile, the water from the funnel basin is drained and the male pupae, which moved into the water through the sieve during the sieving action, are removed from the drainage system through flushing. In some examples, because of the automation described herein, the sieving apparatus may enable separation of hundreds of thousands of pupae per hour.

This illustrative example is given to introduce the reader to the general subject matter discussed herein and the disclosure is not limited to this example. The following sections describe various additional non-limiting examples of sieving apparatuses including sieving devices.

Referring now to FIG. 1, FIG. 1 illustrates a perspective view of a sieving apparatus 1000, according to at least one example. The sieving apparatus 1000 includes a frame 1002, an actuation system 1004, a funnel basin system 1006, and a rinse basin system 1008. The sieving apparatus 1000 can be included as a single station within a process flow that includes upstream and downstream processes. The sieving apparatus 1000 along with the upstream and/or downstream processes can be automated using computer control such as by a computer system 1005. The computer system 1005 can be local to the sieving apparatus 1000, remote from the sieving apparatus 1005, and/or distributed between a remote location and the sieving apparatus 1000. For example, the computer system 1005 can be a remote computing device 1009 that computer interacts with a local control unit 1007 of the sieving apparatus 1000 via a network. In this manner, the remote computing device 1009 can provide instructions to the local control 1007 unit for execution. The computer system 1005 can also provide other instructions to other machines and devices located upstream and downstream from the sieving apparatus 1000. The remote computing device 1009 is described in detail with reference to FIG. 20.

The local control unit 1007 may include a processing device such as a microprocessor, a digital signal processor ("DSP"), an application-specific integrated circuit ("ASIC"), field programmable gate arrays ("FPGAs"), state machines, or other processing means. Such processing means may further include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

The processing device may include, or may be in communication with, the memory. The memory includes computer-readable storage media, that may store instructions that, when executed by the processing device, cause the processing device to perform the functions described herein as carried out, or assisted, by the processing device. Examples of computer-readable media may include, but are not limited to a memory chip, Read Only Memory ("ROM"), Random Access Memory ("RAM"), ASIC, or any other storage means from which a processing device can read or write information.

The components of each of the actuation system 1004, the funnel basin system 1006, and the rinse basin system 1008 are attached to and supported by the frame 1002. The frame 1002 may be formed in any suitable manner and from any suitable material so as to provide structural support for the systems 1004, 1006, and 1008. For example, the frame 1002 may be formed from metal tubing (e.g., steel, aluminum, etc.) that is welded, bolted, or otherwise attached together. In some examples, the systems 1004, 1006, and 1008 are not attached to the same frame 1002. For example, the funnel basin system 1006 and the rinse basin system 1008 can be disposed at adjacent stations in the process flow and the actuation system 1004 can move between the adjacent stations to perform the techniques described herein.

Beginning with the actuation system 1004, the actuation system 1004 in this example includes a sieving device 100 (e.g., a sieving container), a rotational actuator 1010, a lifting actuator 1012, and a lateral actuator 1014. Together the rotational actuator 1010, the lifting actuator 1012, and the lateral actuator 1014 manipulate spatial position and orientation of the sieving device 100 with respect to the funnel basin system 1006 and the rinse basin system 1008. For example, as described in detail herein, the lifting actuator 1012 moves the sieving device 100 vertically, the lateral actuator 1014 moves the sieving device 100 horizontally, and the rotational actuator 1010 rotates the sieving device 100.

The funnel basin system 1006 includes a funnel basin 1016 and a drainage system 1018 that includes a first valve 1020a, a drain manifold 1022, and a second valve 1020b. The funnel basin 1016 can have any suitable shape and size other than the cylindrical shape shown. At a minimum, the funnel basin 1016 is sized to receive the sieving device 100 and hold a volume of liquid in which the sieving device 100 can be partially submerged. For example, the funnel basin 1016 can be filled with water and the lifting actuator 1012 can move the sieving device 100 vertically into and out of the funnel basin 1016 as part of a sieving action to separate a population of pupae.

In some examples, the funnel basin 1016 includes a bottom that slopes toward a drain disposed at the center of the bottom. The drain is the attachment point between the funnel basin 1016 and the drainage system 1018. The valves 1020 are controllable to selectively direct fluid from the funnel basin 1016. For example, with the second valve 1020b closed, the first valve 1020a can be opened and fluid can be drained from the funnel basin 1016 via the drain manifold 1022. Because the drain manifold 1022 includes a perforated drain tube 1024, small debris such as pupae present in the liquid will be captured inside the perforated drain tube 1024. The second valve 1020b can then be opened to access the debris remaining in the perforated drain tube 1024. In some examples, a second volume of liquid is drained through the drainage system 1018 with both valves 1020 open. This second volume of liquid functions to flush the drainage system 1018, including any additional debris present in the perforated drain tube 1024.

The rinse basin system 1008 includes a rinse basin 1026, a rinse nozzle 1028, and a spill ramp 1030. The rinse basin 1026 can be any suitable basin having any suitable size. In some examples, the rinse basin 1026 includes a drain that empties to sewer system, a biological waste collection system, a specimen collection receptacle, or any other suitable location. When separating a population of pupae, the group of undesirable pupae can be rinsed off of the sieving device 100 and into the rinse basin 1026. This can be achieved by the lateral actuator 1014 moving the sieving device 100 from a position over the funnel basin 1016 to a position over the rinse basin 1026. At this point, the rotational actuator 1010 rotates the sieving device 100 and the rinse nozzle 1028 sprays a liquid such as water on the sieving device 100 to spray off the pupae. If a specimen collection receptacle is being used, these pupae can also be collected. The spill ramp 1030 helps to avoid contamination by directing any spilled water (e.g., that may drop out of sieving device 100) toward the rinse basin 1026.

The sieving apparatus 1000 can include any suitable sensors to manage the operation of the components of the sieving apparatus 1000. For example, position sensors, e.g. rotational encoders, variable resistors, etc., may be used to sense the position of the actuation system 1004. Ultrasonic sensors may be used to sense a water level in the funnel basin 1016. These sensors can provide sensor data (e.g., output) to the computer system 1005.

Figure 2:
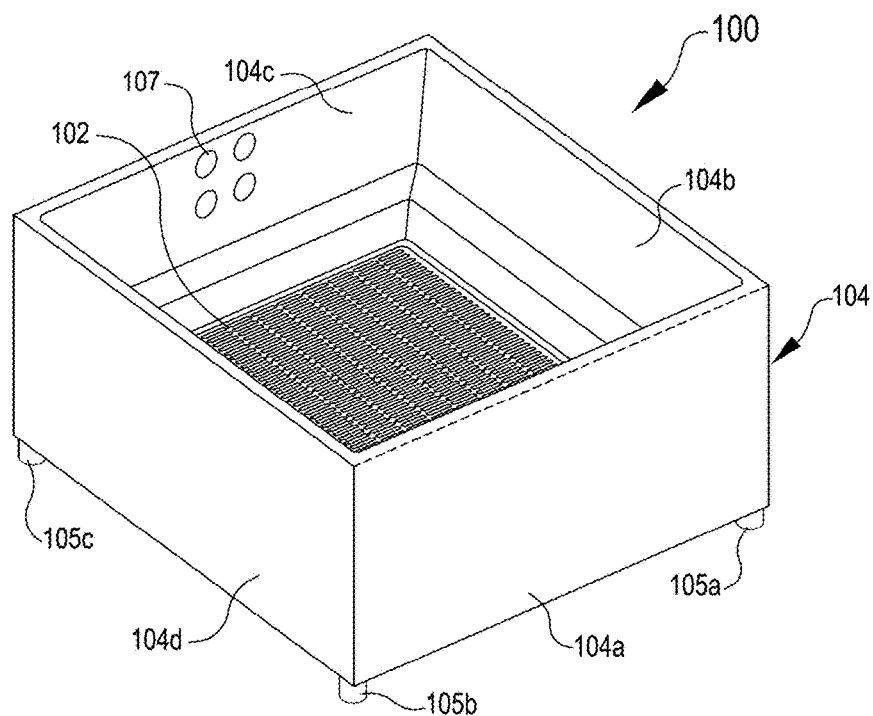
FIG. 2 illustrates a perspective view of a sieving device for use in the sieving apparatus from FIG. 1, according to at least one example.

Details of the sieving device 100 will now be described with reference to FIGS. 2-12. Referring first to FIG. 2, FIG. 2 illustrates a perspective view of the sieving device 100, according to at least one example. The sieving device 100 includes a sieve surface 102 (e.g., a base) held within a sieve rim 104. The sieve rim 104 includes a plurality of walls 104a-104d that together define a volume having a rectangular cross section. In some examples, the sieve rim 104 defines a non-rectangular perimeter (e.g., round, triangular, and any other suitable non-rectangular shape). In some examples, the sieve rim 104 may be formed from one or more pieces of material (e.g., may be formed from a single continuous piece of material or from more than one pieces that have been joined together). Irrespective of the shape of the perimeter, the sieve rim 104 can function to funnel or otherwise direct a liquid (e.g., water) through the sieve surface 102. As the sieving device 100 can be sized for manual use (e.g., 6"×6" square) in some examples, the sieve rim 104 also provides an area whereby an operator can manually grasp and manipulate the sieving device 100. For example, the operator can use her hands to grasp the sieve rim 104 to manipulate the sieving device 100 (e.g., applying an agitating or oscillating motion with respect to an aqueous solution that pushes smaller pupae through the sieve surface 102 and separates larger pupae and/or debris that cannot pass through the sieve surface 102). The sieving device 100 can also be sized for automated use, which may be smaller, larger, or the same size as the manual size. The sieving device 100 can also include an attachment location 107. For example, the attachment location 107 can be used to attach the actuation system 1004 to the sieve rim 104 (e.g., via the rotational actuator 1010). The sieving device 100 also includes a set of feet 105. The feet 105 are attached to the sieve rim 104 and can function to space the sieve surface 102 of off a bottom of a container or other surface. The sieve surface 102 also includes a series of openings 106 which are described in detail with reference to later figures.

Figure 3:
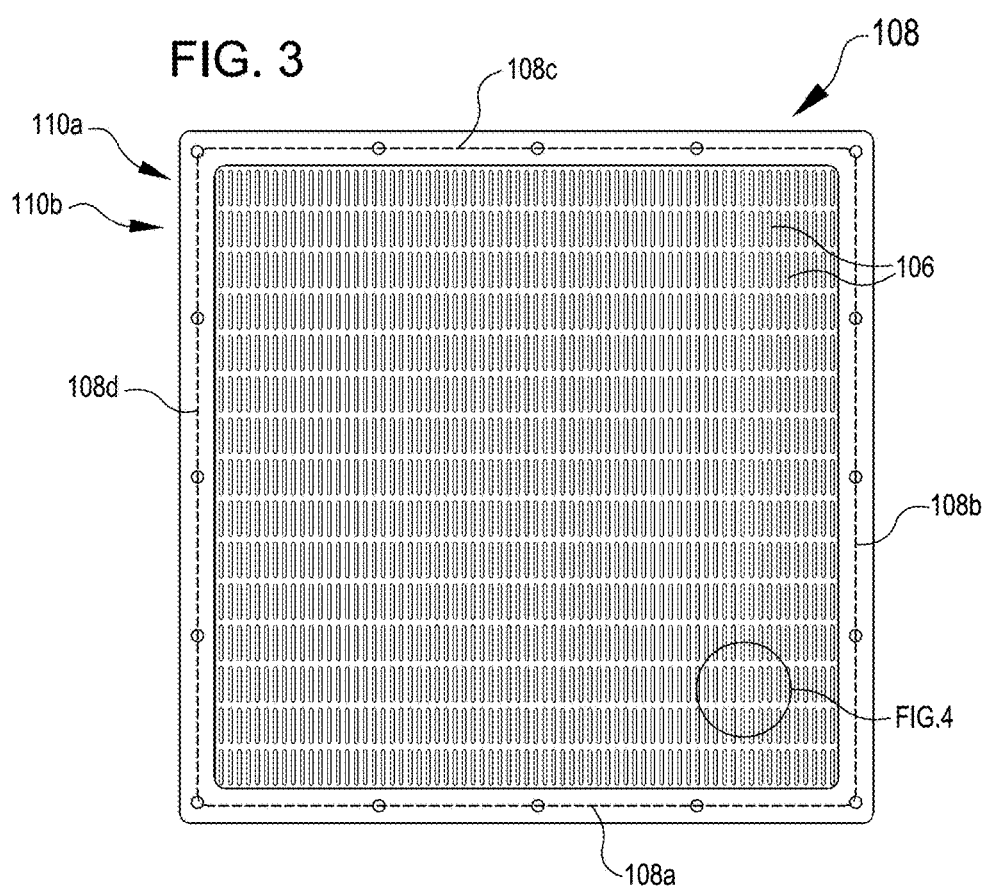
FIG. 3 illustrates a top view of a sieve surface, according to at least one example.

FIG. 3 illustrates a top view of the sieve surface 102, according to at least one example. As illustrated in FIG. 3, the sieve surface 102 can be held within a sieve frame 108. The sieve frame 108 includes a plurality of members 108a-108d that together define a rectangular perimeter. In some examples, the sieve frame 108 has a non-rectangular perimeter. In any event, the cross section of the sieve rim 104 and the cross section of the sieve frame 108 can correspond to enable mounting of the sieve frame 108 within the sieve rim 104. The sieve frame 108 also provides rigidity to the sieve surface 102. In some examples, sieve frames 108 having different sieve surfaces 102 (e.g., different sized openings) can be detachably mounted to the same sieve rim 104, depending on the implementation. For example, a kit can include multiple sieve surfaces 102 having different sized openings 106 that can be independently detachably mounted to the sieve rim 104.

Figure 4:
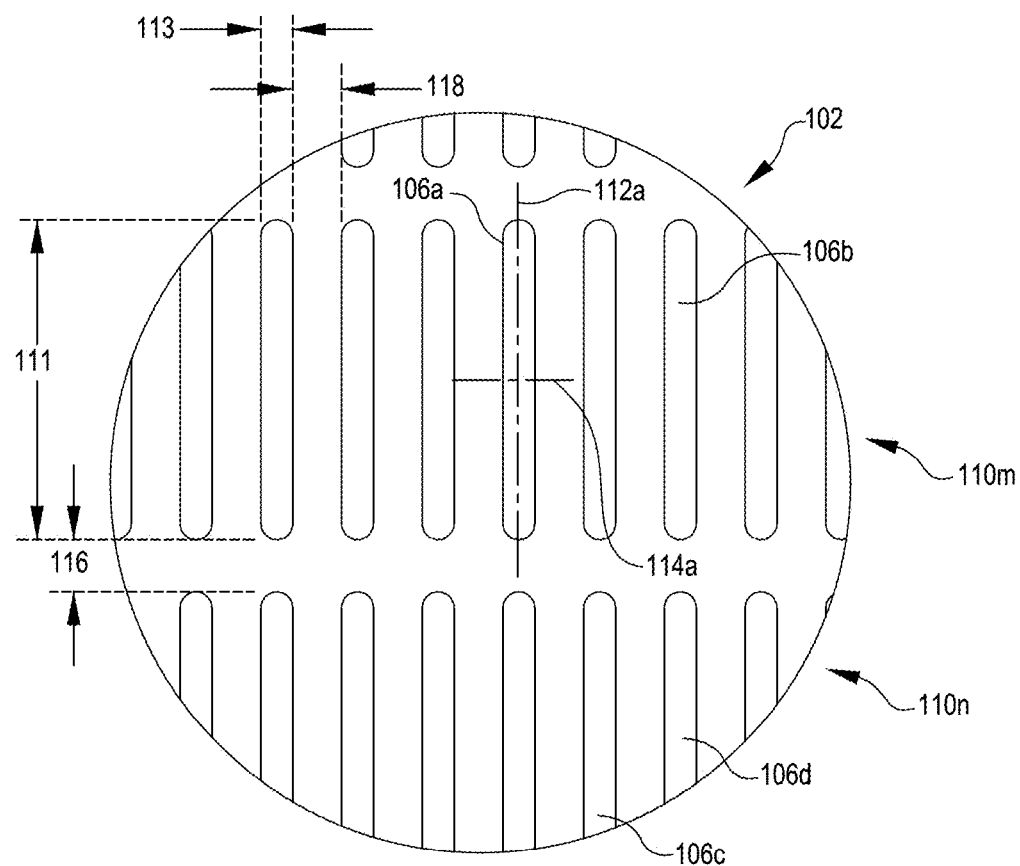
FIG. 4 illustrates a detailed view of the sieve surface from FIG. 3, according to at least one example.

As illustrated in FIG. 4, the openings 106 can be organized into a series of rows 110a-110n including a plurality of openings 106. A few of the rows are labeled (e.g., 110a and 110b). The openings 106 can be repeated within the rows 110 to form a row pattern. The rows 110 can be repeated within the sieve surface 102 to form a sieve surface pattern. The number and dimensions of the rows 110 can be a product of the dimensions of the openings 106, spacing between the openings 106, and the material used to form the sieve surface 102. In some examples, a single row 110 including a plurality of openings 106 is provided. In this example, the single row 110 can extend transversely between members 108b and 108d. The openings 106 of this single row 110 can extend longitudinally between members 108a and 108c.

In some examples, the sieve surface 102 is formed by a plurality of elongate rods laid out between the members 110b and 110d. The ends of these rods can extend between the members 108a and 108c and be held in place by these members 108a and 108c. In this example, the openings 106 can be formed between individual ones of the plurality of elongate rods.

FIG. 4 illustrates a detailed view of the sieve surface 102, according to at least one example. The sieve surface 102 can be defined as having the openings 106, a few of which are labeled. Each opening 106 can have a generally elongate cross section. For example, as illustrated with respect to opening 106a, the cross section can be defined by a length dimension 111 measured along a longitudinal axis 112a of the opening 106a and a width dimension 113 measured along a transverse axis 114a of the opening 106a. The length dimension 111 can be greater than the width dimension 113. As described in detail herein, a generally elongate cross section can enable selection of a smaller width dimension 113 corresponding to the smallest dimension of cephalothorax as compared to square mesh sieves, which are generally sized to the largest dimension of the cephalothorax.

A value of the width dimension 113 can be dependent on the goals of a separation program and characteristics of pupae to be separated. For example, populations of *Aedes aegypti* or *Aedes albopictus* mosquitoes can be separated. Other species of mosquitoes or other populations of insects having a pupae stage can be separated using the sieving device 100 described herein. For example, the sieving device 100, in particular the openings 106, a space dimension 118, and a row dimension 116 may be tailored to the specific insect species.

As described herein, the sieving device 100 can be used to separate any species of insect that has an aquatic pupal phase. In some examples, the value of the width dimension 113 may correspond to a cross-sectional cephalothorax width of a representative insect from a particular insect species. In some examples, the width dimension 113 may range from 800 microns to 1500 microns, which may be appropriate for separating some species of mosquitoes, such as *Aedes aegypti*. Values larger than 1500 microns and smaller than 800 microns may be appropriate for other insect species. In a particular example, the value of the width dimension 113 can be about 1200 microns. In some examples, a value of the length dimension 111 may correspond to a cross-sectional cephalothorax length of a representative insect from the particular insect species. In a particular example, the length dimension 111 may range from 2500 microns to many millimeters (e.g., 12 millimeters), which may be appropriate for separating some species of mosquitoes. Values larger than 12 millimeters and smaller than 2500 may also be appropriate for other insect species.

A value of the length dimension 111 can also be dependent on the goals of the separation program and characteristics of the pupae to be separated. For example, in the example illustrated in FIG. 3, the value of the length dimension 111 is about 10 times greater than the value of the width dimension 113. In some examples, the value of the length dimension 111 can be arbitrarily selected so long as it is greater than a largest cross-sectional dimension (e.g., tip to tail) of a typical pupa which is expected to pass through the opening 106a. Because the width dimension 113 is sized to correspond to a different smaller dimension of the typical pupa, the length dimension 111 will be larger than the width dimension 113.

The rows 110 can be spaced in accordance with the row dimension 116. For example, row 110m including the openings 106a, 106b can be spaced apart from row 110n including the openings 106c, 106d by the row dimension 116. The openings 106 can be spaced in accordance with the space dimension 118. For example, the opening 106a can be spaced apart from the opening 106b by the space dimension 118.

A value of the row dimension 116 may correspond or otherwise be proportional to a cross-sectional cephalothorax dimension of a representative insect of a preselected insect type. For example, the row dimension 116 may have a value that corresponds to a cross-sectional cephalothorax width or length of the representative insect. In this manner, the row dimension 116 may be selected to avoid having material in the sieve surface 102 that could hook or otherwise catch pupae and thereby prevent them from rolling off. In some examples, the row dimension 116 may enable the pupae to roll off the sieve surface 102 (e.g., through the openings 106). In a particular example, the row dimension 116 may range from 1000 microns to 3000 microns. In some examples, the value of the row dimension 116 is greater than 3000 microns or smaller than 1000 microns.

A value of the space dimension 118 may correspond or otherwise be proportional to a cross-sectional cephalothorax dimension of a representative insect of a preselected insect type. For example, like the row dimension 116, the space dimension 118 may have a value that corresponds to a cross-sectional cephalothorax width or length of the representative insect. In this manner, the space dimension 118 may be selected to avoid having material in the sieve surface 102 that could hook or otherwise catch pupae and thereby prevent them from rolling off. In some examples, the space dimension 118 may enable the pupae to roll off the sieve surface 102 (e.g., through the openings 106). In a particular example, the space dimension 118 may range from about 500 microns to 3000 microns. In some examples, the value of the space dimension 118 is greater than 3000 microns or smaller than 500 microns. Depending on the value of the row dimension 116, the value of the space dimension 118, the value of the length dimension 111, and the value of the width dimension 113, an example sieve surface 102 may have between 5-30 openings 106 per square inch. In some examples, the value of the row dimension 116, the value of the space dimension 118, the value of the length dimension 111, and the value of the width dimension 113 are selected to provide sufficient rigidity to the sieving device 100 and a suitable fraction of open area to solid structure (e.g., openings 106 compared to rigid portion of the sieve surface 102), while still preventing entanglement with the pupae.

In some examples, the values of the row dimension 116 and the space dimension 118 are selected to minimize a ratio of solid area to open area across the sieve surface 102. Thus, by placing the openings 106 close together (e.g., a small value of the space dimension 118) and placing the rows 110 close together (e.g., small value of the row dimension 116), a greater quantity of openings 106 and rows 110 can be formed in the sieve surface 102. This can provide for increased throughput and increased yield in a separation program.

In some examples, the values of the row dimension 116 and the space dimension 118 depends on the material selected for the sieve surface 102 and the forming method. The sieve surface 102 can be formed from any suitable material such as metal, plastic, glass, ceramic, acrylic, and other materials having similar properties. The forming technique used to form the sieve surface 102 will depend on the material selected. Example forming techniques include, but are not limited to, laser cutting, water jet cutting, photo-chemical etching, punching, die cutting, milling, additive manufacturing (e.g., three-dimensional printing), molding, casting, stamping, and other similar techniques.

FIGS. 5, 6, and 7 respectively illustrate a side view, a first profile view, and a second profile view of an example mosquito pupa 400 that can be separated using the sieving device 100, according to various examples. The mosquito pupa 400 includes a cephalothorax 402 and an abdomen 404. When in the pupal stage, the mosquito pupa 400 uses its abdomen 404, including a distal portion 404a, as a flipper to move through water 408. The cephalothorax 402 also includes eyes 406, one of which is illustrated and labeled. In the profile view illustrated in FIG. 5, the mosquito pupa 400 can be defined by a cephalothorax width 410 and an overall length 412. In the profile view illustrated in FIG. 6, the mosquito pupa 400 can also be defined by the cephalothorax height 414. Based on the physiological structures of the pupae (e.g., the mosquito pupa 400), the cephalothorax width 410 will be less than the overall length 412. In some examples, the cephalothorax height 414 is greater than the cephalothorax width 410. Thus, the cephalothorax width 410 can represent the narrowest dimension of the largest part (e.g., the cephalothorax 402) of the mosquito pupa 400.

As introduced herein, the value of the length dimension 111 of the openings 106 can be selected based on the overall length 412. For a given pupal population, a minimum value for the length dimension 111 should be greater than the overall length 412 of the largest pupa in the population. In some examples, a value of the length dimension 111 is much greater the overall length 412 of the largest pupa (e.g., an order of magnitude of 10 to 100 times greater).

As introduced herein, the value of the width dimension 113 of the openings 106 can be selected based on the cephalothorax width 410. For example, assume for a moment that a goal of a separation program is to separate male mosquito pupae from female mosquito pupae. In this example, if an example male population has an average cephalothorax width 410 of 1100 microns and an example female population has an average cephalothorax width 410 of 1400 microns. Given this difference of 300 microns between the average cephalothorax widths and given a difference of about 50 microns between a female mosquito with the smallest cephalothorax width 410 (e.g., 1250 microns) in the female population and a male mosquito pupa with the largest cephalothorax width 410 (e.g., 1200 microns) in the male population, a value for the width dimension 113 can be selected to give a high probability of separation. In this example, a value of 1200-1225 microns for the width dimension 113 can be suitable. Of course, other values would be appropriate for other populations of insects having cephalothoraxes of different sizes.

In the view illustrated in FIG. 5, the mosquito pupa 400 is oriented in a natural orientation, one in which the mosquito pupa 400 will naturally orient when located within the water 408. In this orientation, the mosquito pupa 400 is able to obtain oxygen at the surface of the water 408 via respiratory trumpets (not shown) that extend from an upper portion of the cephalothorax 402 (e.g., near the upper surface of the water 408). This orientation may be referred to as a "tail down orientation" because the distal portion 404a of the abdomen 404 (e.g., a tail) points down.

FIG. 8 illustrates a side view of the mosquito pupa 400 passing through the opening 106 in the sieve surface 102, according to at least one example. In the example illustrated in FIG. 8, the mosquito pupa 400 is oriented in the tail down orientation as the mosquito pupa 400 passes through the opening 106.

FIGS. 9 and 10 respectively illustrate a first mosquito pupa 400a in a first orientation and a second orientation with respect an opening 106, according to various examples. In particular, the first mosquito pupa 400a is shown passing through the opening 106. This is because the cephalothorax width 410 of a first cephalothorax 402a is less than a value of the width dimension 113. The first orientation of the first mosquito pupa 400a illustrated in FIG. 9 is an example of the tail down orientation illustrated in FIGS. 5 and 9. The second orientation of the first mosquito pupa 400a illustrated in FIG. 10 is an example of a tail up orientation. This may constitute a rotation of about 180 degrees.

FIGS. 11 and 12 respectively illustrate a second mosquito pupa 400b in a first orientation and a second orientation with respect an opening 106, according to various examples. In particular, the second mosquito pupa 400b is shown as being prevented from passing the opening 106. This is because the cephalothorax width 410 of a second cephalothorax 402b is greater than a value of the width dimension 113. The first orientation of the second mosquito pupa 400b illustrated in FIG. 11 is an example of the tail down orientation illustrated in FIGS. 4 and 7. The second orientation of the second mosquito pupa 400b illustrated in FIG. 12 is an example of the tail up orientation. This may constitute a rotation of about 180 degrees.

In some examples, the openings 106 of the sieve surface 102 are sized such that the first mosquito pupae 400a can pass through the openings 106 and the second mosquito pupa 400b are prevented from passing through the openings 106. For example, the first mosquito pupae 400a may be male pupae and the second mosquito pupae 400b may be female pupae. In some examples, the first mosquito pupae 400a is a first set of male (or female) pupae and the second mosquito pupae 400b is a second set of male (or female) pupae.

In some examples, the openings 106 of the sieve surface 102 are sized such that the first mosquito pupae 400a can pass through the openings 106 in any one of the tail down or tail up orientations and the second mosquito pupae 400b are prevented from passing through in any orientation. In some examples, the openings 106 are sized such that the first mosquito pupae 400a may pass through in other orientations as well (e.g., head down or abdomen down).

FIGS. 13-17 illustrate example states of the sieving apparatus 1000 as the sieving apparatus performs an automated sieving process, according to various examples. Execution of the automated sieving process enables separation and downstream processing of a population of pupae such as mosquito pupae. The state changes of the components of the sieving apparatus 1000 illustrated in FIGS. 13-17 may be performed under the management of the computer system 1005.

FIG. 13 illustrates a detailed view of an example state 1300 of the sieving apparatus 1000, according to at least one example. In the state 1300, the sieving device 100 is disposed vertically above the funnel basin 1016. The lifting actuator 1012 may include any suitable structure and controls to enable the vertical movement of the sieving device 100 described herein. For example, the lifting actuator 1012 may include a vertical carrier 1032 attached to the frame 1002 via a vertical rail 1034. The rotational actuator 1010 is disposed between and attaches to the vertical carrier 1032 and the sieving device 100. The vertical carrier 1032 can include an electric motor (e.g., servomotor) or other suitable actuator device (e.g., hydraulic actuators, pneumatic actuators, thermal actuators, etc.) configured to move the vertical carrier 1032 vertically along the vertical rail 1034. In particular, the lifting actuator 1012 may move the sieving device 100 into and out of the funnel basin 1016 as part of the sieving process, as illustrated by the vertical arrow 1036. Operation of the lifting actuator 1012 can be managed by the computer system 1005.

As illustrated in the state 1300, the sieving process may include filling the funnel basin 1016 with a liquid such as water. A fill nozzle may be disposed adjacent to the funnel basin 1016 in order to dispense the liquid. In some examples, the fill nozzle is a puck dispensing spout to enable adding fixed volumes of the liquid. Operation of the fill nozzle can be managed by the computer system 1005. After or before the funnel basin 1016 has been filled with water or while the funnel basin 1016 is being filled with water, the lifting actuator 1012 can be actuated to move the sieving device 100 down toward the funnel basin 1016 so as to submerge the sieve surface 102 in the water. A population of pupae may be added to the sieving device 100 (e.g., within the sieve rim 104). The population of pupae may include pupae of different sizes, of different sexes, of different species, and/or any combination of the foregoing. In some examples, the population of pupae includes males and females of the same species. A conveyor system or other automated process may add the population of pupae to the sieving device 100. Addition of the population of pupae can be managed by the computer system 1005. Any suitable number of pupae may be added to the sieving device 100. For example, when the sieve rim 104 is about 8"×8" square, around 6,000 mosquito pupae may be included in the population. In some examples, the population of pupae are treated with a larvicide prior to being added to the sieving device 100. This ensures any larvae still present in the population are dead prior to going through the sieving process.

Once the mosquito pupae have been added, the lifting actuator 1012 can be actuated to perform a sieving action that causes separation of the population of pupae 1206. For example, the lifting actuator 1012 can be actuated between two vertical elevations, at one of which the sieve surface 102 is submerged in the water and at the other of which the sieve surface 102 is removed the water. This sieving action of dunking the sieve surface 102 into and out of the water functions to force the pupae into two groups (e.g., a first group that will fit through the sieve surface 102 and remain the water in the funnel basin 1016 and a second group that will not fit through the sieve surface 102 and remain in the sieving device 100). This action can be repeated any suitable number of cycles (e.g., predetermined, dynamic based on vision or weight, etc.). For example, an optical system including a camera can output image data as the sieving device 100 is moved. The computer system 1005 processes this image data to determine whether an expected number of pupae have been separated. In some examples, three cycles are performed. In some examples, a complete cycle may take about two seconds (e.g. one second down and one second up).

In some examples, instead of manipulating the elevation of the sieve surface 102 relative to the water, the water level within the funnel basin 1016 can be adjusted relative to the sieve surface 102. For example, a pump system may circulate the same water into and out of the funnel basin 1016. In other examples, the pump system may pump out dirty water and replace the dirty water with clean water. Operation of the pump(s) can be managed by the computer system 1005.

In some examples, the sieving action that causes separation of the population of pupae 1206 may include oscillating, agitating, shaking, and/or otherwise moving the sieving device 100 (e.g., rolling). Such movements may include raising and lowering an elevation of the sieving device 100, translating the sieving device 100 forward and backward, translating the sieving device side-to-side, rotating on one or more ends of the sieving device 100 with respect to other ends, rolling the sieving device 100, performing any combination of the foregoing, and performing any other change to orientation and position of the sieving device 100. One or more of these actions can be performed simultaneously, in a predefined order, or in any other manner that causes separation of the population of pupae 1206.

The sieving device 100 can be oscillated, agitated, and/or shaken when at least some liquid is present within the sieve rim 104. In some examples, the sieving device 100 is oscillated, agitated, and/or shaken when little to no liquid is present in the sieve rim 104. For example, when a population of pupae is suspended in an aqueous solution in a pupae container, the sieving action may be performed as the population of pupae is transferred from the pupae container to the sieving device 100. In this example, the sieving device 100 may be oscillated, agitated, shaken, and/or otherwise moved in a manner that causes the population of pupae to move within the sieving device 100 and/or causes the aqueous solution in which the pupae are originally suspended or other aqueous solution to move. In this manner, the sieving action may cause separation of the population of pupae. In some examples, an additional sieve surface 102 can be used to separate out other materials, e.g., debris that might be present with the pupae. Any suitable number of sieving surfaces 102 can be used to separate a set of insects into any suitable number of groups.

Continuing with the sieving process, as illustrated in the state 1300, the first valve 1020a can be opened after the sieving action has finished. The second valve 1020b remains closed. Operation of the valves 1020 can be managed by the computer system 1005. This results in the water from the funnel basin 1016 emptying through the perforated drain tube 1024, into the drain manifold 1022, and out of a drain manifold opening 1038. The first group of pupae that remained in the water will remain in the perforated drain tube 1024. This is because openings in the perforated drain tube 1024 are sized smaller than the pupae (e.g., less than 900 microns). After the water has drained from the funnel basin 1016, a second volume of water is added to the funnel basin 1016 to continue to rinse the funnel basin 1016 and to further consolidate the first group of pupae into the perforated drain tube 1024. After this second volume of water has flushed through the funnel basin 1016 and the drainage system 1018, the second valve 1020b is opened to dispense the consolidated first group of pupae into a container for downstream processing. With both valves 1020 open, a third volume of water is added to the funnel basin 1016 to further flush the funnel basin 1016 and the drainage system 1018.

The valves 1020 can be any suitable inline valve such as a ball valve, a butterfly valve, a gate valve, and other similar inline valves. The valves 1020 may include actuators 1021 configured to open and close the valves 1020 in response to a signal (e.g., a control signal from the computer system 1005).

Figure 14:
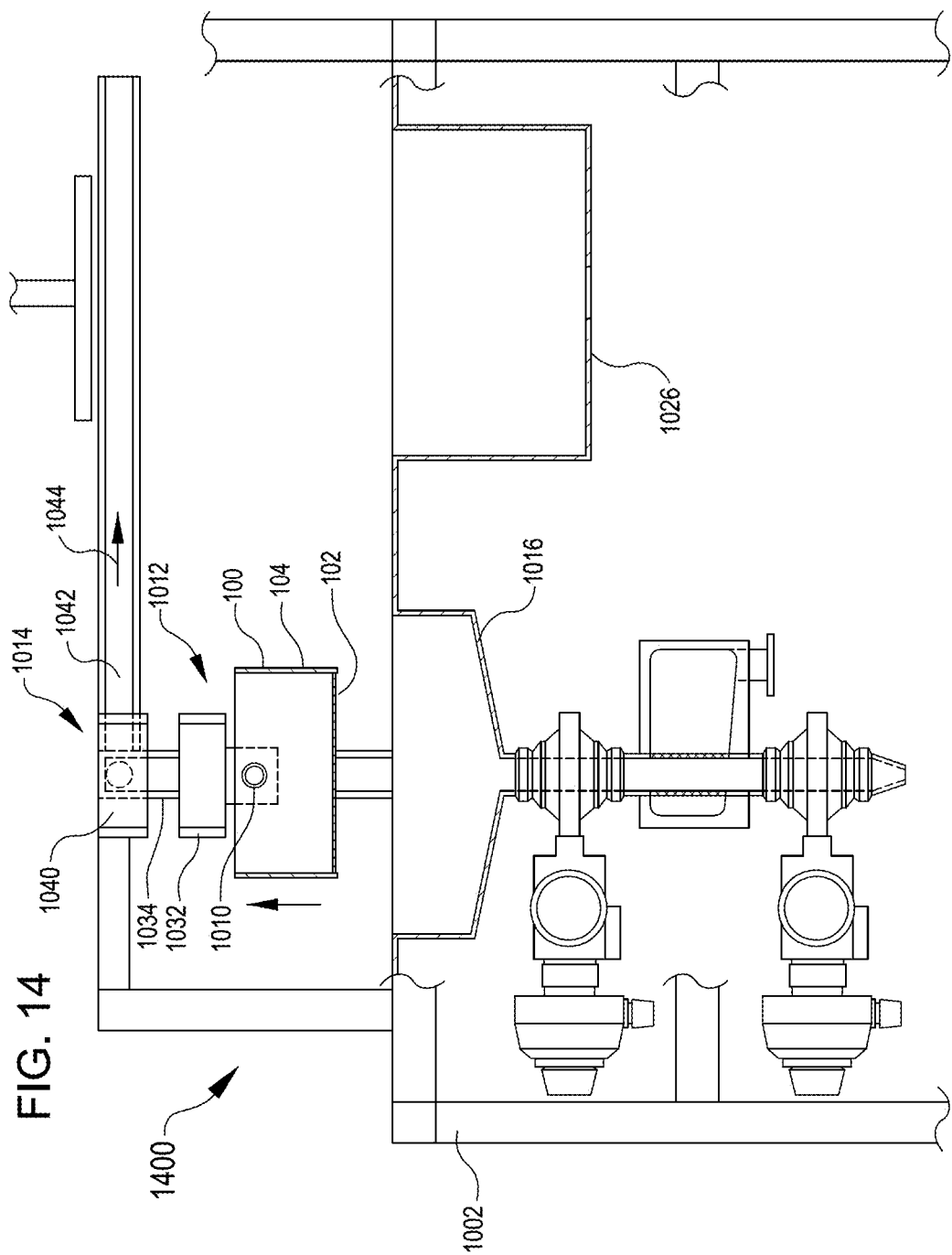
FIG. 14 illustrates a detailed view of an example state of the sieving apparatus from FIG. 1, according to at least one example.

FIG. 14 illustrates a detailed view of an example state 1400 of the sieving apparatus 1000, according to at least one example. Between the states 1300 and 1400, the sieving device 100 has been raised vertically out of the funnel basin 1016. For example, the lifting actuator 1012 has raised the sieving device 100. In the state 1400, the second group of pupae is disposed in the sieve device 100 (e.g., those that could not fit through the sieve surface 102). In the state 1400, the sieving apparatus 1000 is prepared to move the sieving device 100 from a position over the funnel basin 1016 to a position over the rinse basin 1026.

The lateral actuator 1014, for example, can be used to perform this change in position of the sieving device 100. The lateral actuator 1014 may include any suitable structure and controls to enable the lateral movement (e.g., sideways movement other than vertical which may include horizontal and/or angled) of the sieving device 100 described herein. For example, the lateral actuator 1014 may include a lateral carrier 1040 attached to the frame 1002 via a horizontal rail 1042. In some examples, the lateral carrier 1040 is attached to the vertical rail 1034 of the lifting actuator 1012. In this manner, the vertical rail 1034, the vertical carrier 1032, the rotational actuator 1010, and the sieving device 100 all translate laterally (e.g., horizontally) together when the lateral actuator 1014 is actuated. The lateral carrier 1040 can include an electric motor (e.g., servomotor) or other suitable actuator device (e.g., hydraulic actuators, pneumatic actuators, thermal actuators, etc.) configured to move the lateral carrier 1040 laterally along the horizontal rail 1042. In particular, the lateral actuator 1014 may move the sieving device 100 between the funnel basin 1016 and the rinse basin 1026 as part of the sieving process, as illustrated by the horizontal arrow 1044. Operation of the lateral actuator 1014 can be managed by the computer system 1005.

Figure 15:
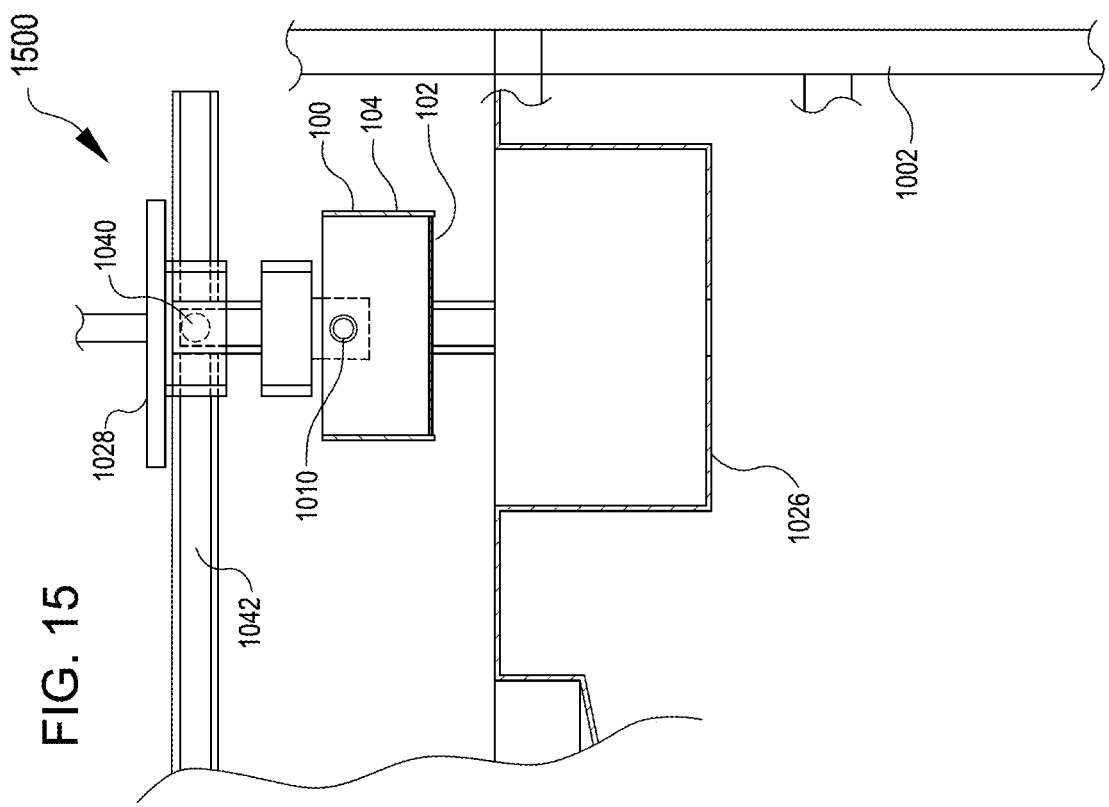
FIG. 15 illustrates a detailed view of an example state of the sieving apparatus from FIG. 1, according to at least one example.

FIG. 15 illustrates a detailed view of an example state 1500 of the sieving apparatus 1000, according to at least one example. Between the states 1400 and 1500, the sieving device 100 has been translated horizontally from a position over the funnel basin 1016 to a position over the rinse basin 1026. The lateral actuator 1014 causes the movement between the states 1400 and 1500.

Figure 16:
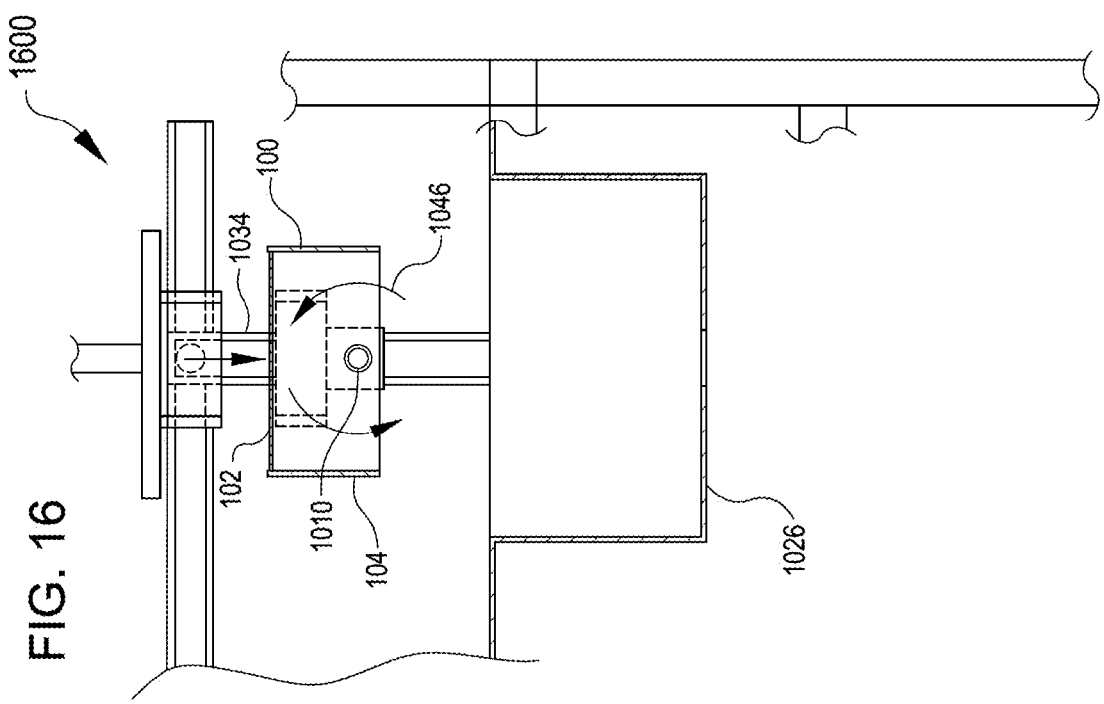
FIG. 16 illustrates a detailed view of an example state of the sieving apparatus from FIG. 1, according to at least one example.

FIG. 16 illustrates a detailed view of an example state 1600 of the sieving apparatus 1000, according to at least one example. Between the states 1500 and 1600, the sieving device 100 has been rotated by the rotational actuator 1010.

For example, the rotational actuator 1010 can include a shaft by which the rotational actuator 1010 is attached to the sieving device 100. A rotational axis may extend through the shaft such that the rotational actuator 1010 can rotate the sieving device 100 about the rotational axis. The rotational actuator 1010 is attached to the vertical carrier 1032 and thereby moves vertically and horizontally as the lifting actuator 1012 and the lateral actuator 1014 are actuated. In some examples, the rotational actuator 1010 is offset laterally from the vertical rail 1034. The rotational actuator 1010 may include any suitable structure and controls to enable the rotational movement (e.g., rotation about the rotational axis) of the sieving device 100 described herein. For example, the rotational actuator 1010 may include an electric motor (e.g., servomotor) or other suitable actuator device (e.g., hydraulic actuators, pneumatic actuators, thermal actuators, etc.) configured to rotate the sieving device 100 relative to the frame 1002 as part of the sieving process, as illustrated by rotational arrows 1046. Operation of the rotational actuator 1010 can be managed by the computer system 1005.

FIG. 17 illustrates a detailed view of an example state 1700 of the sieving apparatus 1000, according to at least one example. Between the states 1600 and 1700, the rinse nozzle 1028 has been actuated to begin rinsing the sieving device 100. For example, the rinse nozzle 1028 can include a valve and actuator assembly that is controlled by the computer system 1005. The rinse nozzle 1028 can emit high pressure liquid such as water in the direction of the sieving device 100. The water functions to rinse the second group of pupae of off the sieving device 100. In particular, the water rinses the sieve surface 102 and the sieve rim 104. The rinsing can be performed for any suitable period time, which may be predetermined or dynamic. The pupae of the second group and the water drains into the rinse basin 1026 and out of drain 1048. In some examples, the second group of pupae can be transferred to a container after they pass through the drain 1048 for further downstream processing. In some examples, the second group of pupae are filtered from the rinse water and disposed of.

In some examples, the system sieving apparatus 1000 can be used for separating the first group of pupae and the second group of pupae into one or more subgroups. For example, sieving devices 100 having sieve surfaces 102 with differently sized openings 106 can be used in sequence to further refine the separation of the pupae. For example, the second group of pupae which did not pass through the first sieve surface 102 can be sieved again using a sieve surface with larger openings than the first surface 102. The sieving process can be repeated to sort precisely by size differential. This process can also be performed in reverse, where the largest sieve surface 102 is used first, and sequentially moving to smaller and smaller sieve surfaces 102. In some examples, an additional sieve surface 102 can be used to separate out other materials, e.g., debris that might be present with the pupae. Any suitable number of sieving surfaces 102 can be used to separate a set of insects into any suitable number of groups.

Figure 21A:
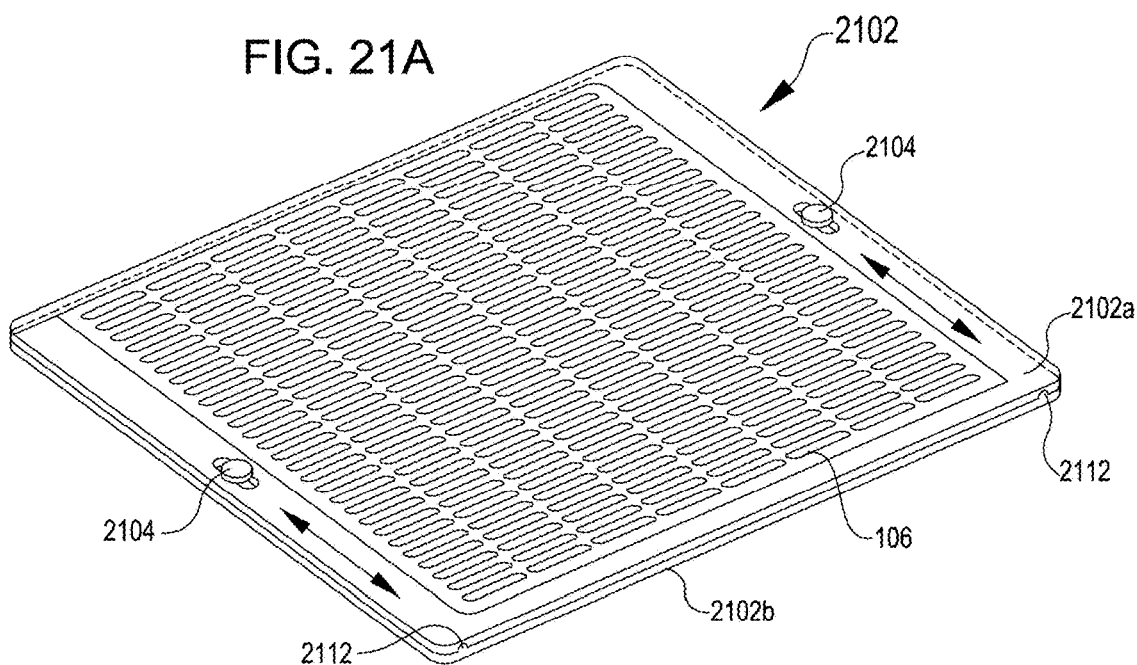
FIG. 21A illustrates a top view of an example sieve surface, according to at least one example.
Figure 21B:
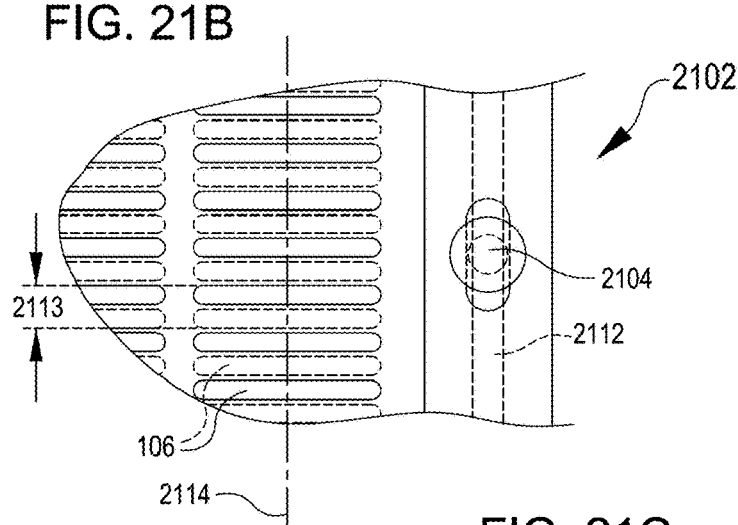
FIG. 21B illustrates a first detailed view of the sieve surface of FIG. 21A, according to at least example.
Figure 21C:
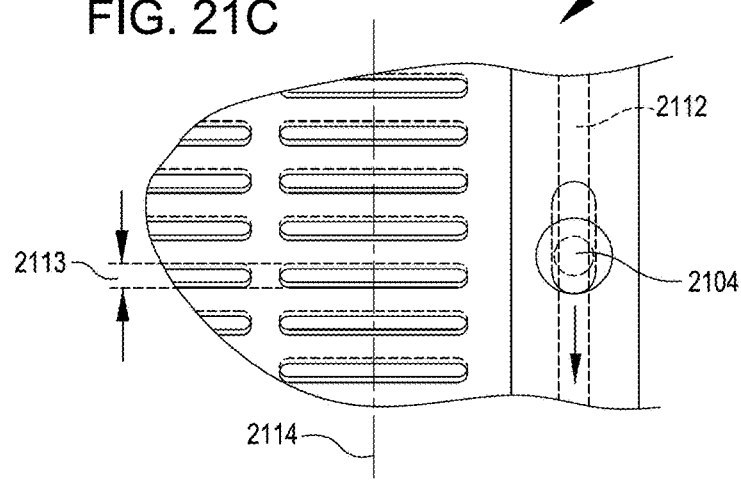
FIG. 21C illustrates a second detailed view of the sieve surface of FIG. 21A, according to at least example.
Figure 22A:
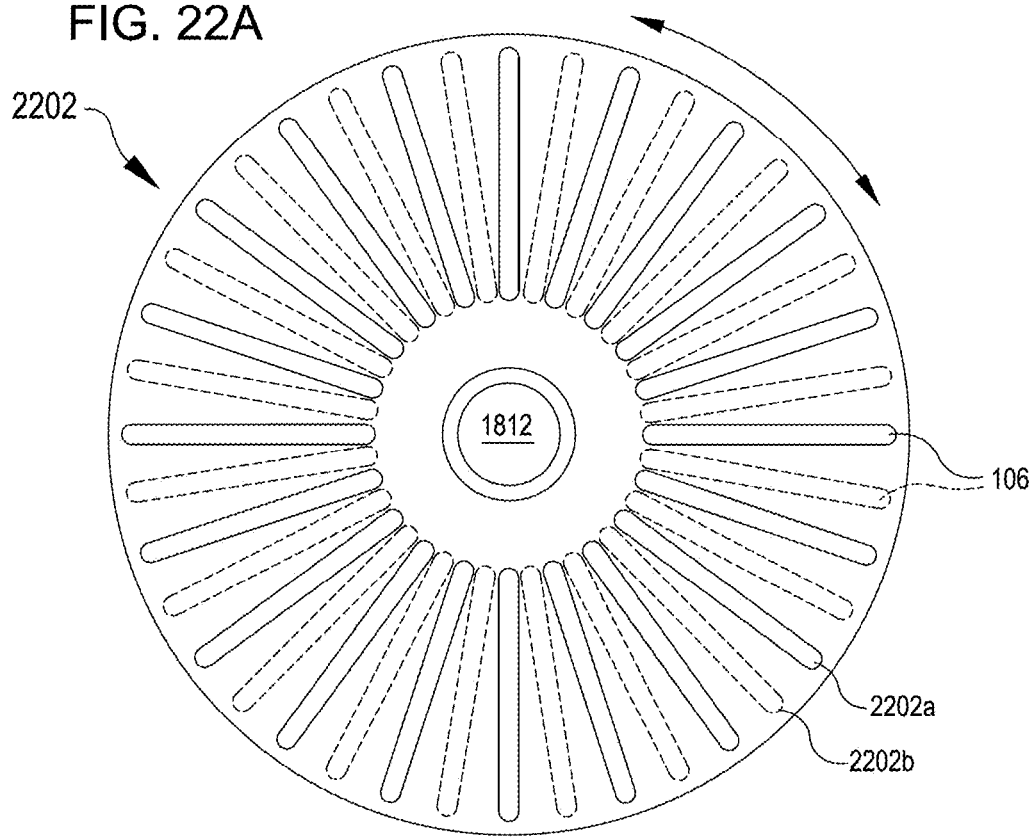
FIG. 22A illustrates an adjustable sieve surface in a first state, according to at least one example.
Figure 22B:
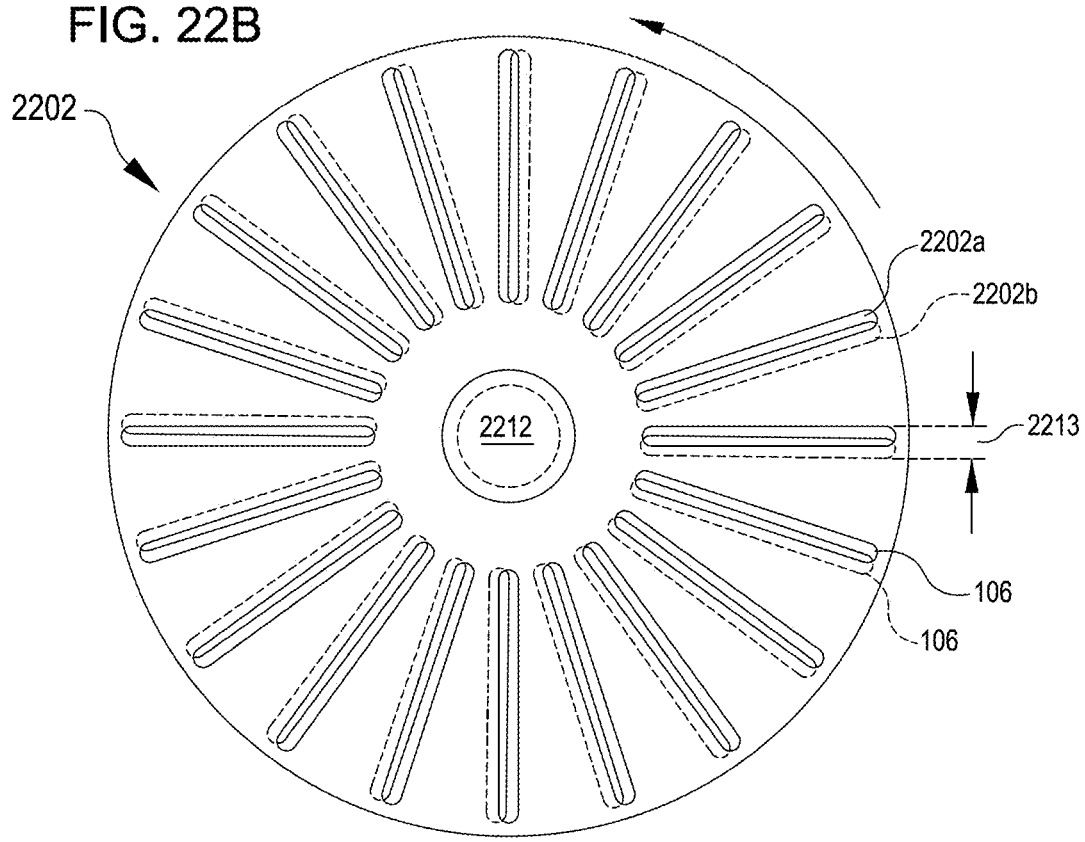
FIG. 22B illustrates the adjustable sieve surface of FIG. 22A in a second state, according at least one example.

For example, as illustrated in FIGS. 21 and 22, in some examples, a single sieving device 100 can include an adjustable sieve surface 2102 and 2202. As shown in FIG. 21, the adjustable sieve surface 2102 can include two or more sieve surfaces 2102a and 2102b positioned on top of each other (e.g., a top sieve surface 2102a and a bottom sieve surface 2102b). The two or more sieve surfaces 2102 may be held adjacent to each other via an alignment structure 2112 (e.g., a set of tongue and groove structures, a tab and channel, a pair of parallel walls configured to retain the sieve surfaces 2102, and any other suitable structure configured to align two or more planar surfaces (e.g., two or more sieve surfaces 2102) and enabling slidable movement of the two or more sieve surfaces 2102). At least one of the sieve surfaces 2102 (e.g., the sieve surface 2102a) is configured to slide with respect to the other sieve surface(s) 2102 (e.g., the sieve surface 2102b) so as to expand and contract a value of the width dimension 2113 of the openings 106. When openings 106 of the sieve surfaces 2102 are aligned with each other, the value of the width dimension 2113 is the greatest. When one of the sieve surfaces 2102 is moved with respect to the other sieve surface(s) 2102, the value of the width dimension 2113 may get smaller.

For example, as illustrated in FIGS. 21B and 21C, a first sieve surface 2102a may be configured to slide along the transverse axis 2114 with respect to a second sieve surface 2102b at least until a value of the width dimension 2113—measured between openings in the first sieve surface 2102a and openings in the second sieve surface 2102b—is about half the value of the width dimension 2113 measured when the openings 106 of the first and second sieve surfaces 2102a, 2102b are aligned. In some examples, the first sieve surface 2102a may be transversely moveable with respect to the second sieve surface 2102b within some range that is less than the value of the width dimension 2113 measured when the openings 106 of the first and second sieve surfaces 2102a, 2102b are aligned. In this manner, movement (e.g., sliding) of the first sieve surface 2102a may contract the openings 106. In some examples, the adjustable sieve surface 2102 may include a knob 2104 or other structure configured to control the slidable movement of the sieve surfaces 2102a, 2102b. In some examples, the knob 2104 can gripped by a user to slide at least one of the first sieve surface 2102a or the second sieve surface 2102b. For example, the knob 2104 may be connected to the second sieve surface 2102b and, as such, may be configured to slide the second sieve surface 2102b with respect to the first sieve surface 2102a.

As illustrated in FIG. 22, in some examples, a single sieving device 100 can include an adjustable sieve surface 2202 that includes two or more sieve surfaces 2202a, 2202b stacked on top of each other and held in a rotary relationship. Thus, instead of a first sieve surface (e.g., 2102a) being configured to translate with respect to a second sieve surface (e.g., 2102b), the first sieve surface 2202a can be configured to rotate with respect to the second sieve surface 2202b so as to adjust values of the width dimension 2213 of the openings 106. For example, such rotation may be achieved by connecting the two or more sieve surfaces 2202a, 2202b via a shaft 2212 or other alignment structure that extends through a center point of the sieve surfaces 2202a, 2202b.

A pattern of the openings 106 in the first sieve surface 2202a can be the same as a pattern of the openings 106 in the second sieve surface 2202b. In some examples, the patterns on the two sieve surfaces 2202a, 2202b are different.

In some examples, the sieving device 100, including the adjustable sieve surface (e.g., 2102 or 2202), may be used in a process for separating artifacts of various sizes (e.g., insects in various stages, insects of various species, random debris, any combination of the foregoing, etc.). For example, with reference to FIGS. 21, the process may begin by translating a first sieve surface 2102a with respect to a second sieve surface 2102b into a first overlapping position. In the first overlapping position, values of the openings 106 may be the smallest and allow debris to pass through the openings 106, but prevent larvae and pupae from passing therethrough. From the first overlapping position, the first sieve surface 2102a can be translated with respect to the second sieve surface 2102b so as to widen the openings to a second overlapping position. In the second overlapping position, values of the openings 106 may be suitably sized to allow larvae to pass through the openings 106, but prevent pupae from passing therethrough. From the second overlapping position, the first sieve surface 2102a can be translated with respect to the second sieve surface 2102b so as to widen the openings 106 to a third overlapping position. In the third overlapping position, values of the openings 106 may be suitably sized to allow male pupae to pass through the openings 106, but prevent female pupae from passing therethrough. From the third overlapping position, the first sieve surface 2102a can be translated with respect to the second sieve surface 2102b so as to widen the openings 106 to a fourth overlapping position. In the fourth overlapping position, values of the openings 106 may be suitably sized to allow female pupae to pass through the openings 106. In this manner, the openings 106 may be gradually widened so as to split up an initial population into any suitable number of sub-samples (e.g., debris, larvae, male pupae, and female pupae).

FIGS. 18 and 19 illustrate example flow diagrams showing respective processes 1800 and 1900, as described herein. These processes 1800 and 1900 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program including a plurality of instructions executable by one or more processors. The computer-readable storage medium is non-transitory.

FIG. 18 illustrates an example flow diagram illustrating the example process 1800 for separating a population of pupae based on size, according to at least one example. The process 1800 can be performed using the sieving apparatus 1000 operating under the management of the computer system 1005.

The process 1800 begins at 1802 by instructing addition of a population of mosquito pupae to a sieving device. In some examples, the sieving device is at least partially submerged in water held within a first basin. In some examples, instructing addition of the population of mosquito pupae to the sieving device includes instructing a human operator to add the population of mosquito pupae or causing an automated device to add the population of mosquito pupae. In some examples, the sieving device includes a sieve rim to which the sieve surface is attached. The sieve rim can form a wall portion of the sieving device. The sieve surface can form a bottom portion of the sieving device opposite an open portion of the sieving device.

At 1804, the process 1800 causes a lifting actuator that is attached to the sieving device to cycle between a first elevation and a second elevation. Such cycling may cyclically submerge a sieve surface of the sieving device in the water held within the first basin. In some examples, the population of mosquito pupae is separated into a first group of mosquito pupae and a second group of mosquito pupae based at least in part on the cycling.

In some examples, the sieve surface includes a first side and a second side. A set of openings can be formed in the sieve surface so as to define a set of pathways extending between the first side and the second side. Individual openings of the set of openings can be defined by a length dimension and a width dimension. The length dimension can be measured along a longitudinal axis of a respective opening. The width dimension can be measured along a transverse axis of the respective opening. In some examples, the width dimension of the individual openings corresponds to a cephalothorax width of a representative mosquito pupa of the population of mosquito pupae. The length dimension can be greater than the width dimension.

At 1806, the process 1800 causes a valve to open to drain the water from the first basin. In some examples, the first group of mosquito pupae is disposed in the water in the first basin.

In some examples, the valve is a first valve in fluid communication with a second valve via a drain pipe. A portion of the drain pipe can include an opening extending into a manifold. The water can drain via the opening and through the manifold.

In some examples, the process 1800 further includes, after causing the first valve to open, causing a second valve to open to obtain access to the first group of mosquito pupae. In this example, the first group of mosquito pupae is prevented from passing through the opening.

At 1808, the process 1800 causes a lateral actuator that is attached to the sieving device to move the sieving device from a first position adjacent to the first basin to a second position adjacent to a second basin. In some examples, the second group of mosquito pupae is disposed in the sieving device.

At 1810, the process 1800 causes a rotational actuator to rotate the sieving device about a rotational axis from a first orientation to a second orientation. This may be performed when the sieving device is at the second position. In some examples, in the first orientation, a sieve surface of the sieving device is disposed below an opening of the sieving device. In some examples, in the second orientation, the sieve surface is disposed above the opening of the sieving device.

At 1812, the process 1800 instructs removal of the second group of mosquito pupae from the sieving device. This may be performed when the sieving device is in the second orientation. In some examples, instructing removal of the second group of mosquito pupae from the sieving device includes causing a rinse nozzle to spray the sieving device. The sieving device can be disposed between the rinse nozzle and the second basin when in the second position.

FIG. 19 illustrates an example flow diagram illustrating the example process 1900 for separating a population of pupae based on size, according to at least one example. The process 1900 can be performed using the sieving apparatus 1000 operating under the management of the computer system 1005.

The process 1900 begins at 1902 by causing an actuation system that is attached to a sieving device to cycle between a first elevation and a second elevation. In some examples, this may cyclically submerge a sieve surface of the sieving device in a liquid held within a basin. The basin can be disposed below the sieving device. In some examples, a population of pupae present in the liquid is separated into a first group of pupae and a second group of pupae as a result of the cycling.

At 1904, the process 1900 causes a valve to open to drain the liquid from the basin. In some examples, the first group of pupae is disposed in the liquid.

At 1906, the process 1900 causes the actuation system to move the sieving device from a first position over the basin to a second position other than over the basin. In some examples, the second group of pupae is disposed in the sieving device. In some examples, the basin is a first basin. In this example, the second position is a position over a second basin disposed adjacent to the first basin. In this example, when the sieving device is at the second position, the process 1900 further includes causing the actuation system to rotate the sieving device about a rotational axis from a first orientation to a second orientation. The process 1900 further includes, when the sieving device is in the second orientation, instructing removal of the second group of pupae from the sieving device. In some examples, instructing removal of the second group of pupae includes causing a spray nozzle to spray the sieving device to remove the second group of pupae.

In some examples, the process 1900 further includes causing a first valve to open to drain the liquid from the basin. The liquid may pass through a perforated drain tube disposed within a drain manifold prior to draining from the drain manifold. In some examples, the process 1900 further includes, after the liquid has drained from the drain manifold, causing a second valve disposed downstream from the perforated drain tube to open. In this example, the first group of pupae is located in the perforated drain tube. In some examples, the process 1900 further includes instructing flushing of the perforated drain tube to move the first group of pupae from the perforated drain tube into a container located downstream from the second valve. In some examples, instructing flushing of the perforated drain tube includes, when the second valve is open causing the first valve to open, and causing a fill nozzle to add a different volume of the liquid to the basin.

FIG. 20 illustrates an example of the computer system 1005, in accordance with at least one example. The computer system 1005 includes the local control unit 1007 in communication with the remote computing device 1009 via communication link 2006. The remote computing device 1009 illustrated in FIG. 20 includes a processor 2002 and a memory 2004.

The processor 2002 may be implemented as appropriate in hardware, computer-executable instructions, firmware, or combinations thereof. Computer-executable instruction or firmware implementations of the processor 2002 may include computer-executable or machine-executable instructions written in any suitable programming language to perform the various functions described.

In some examples, the processor 2002 may include a microprocessor, a DSP, an ASIC, FPGAs, state machines, or other processing means. Such processing means may further include programmable electronic devices such as PLCs, PICs, PLDs, PROMs, EPROMs, EEPROMs, or other similar devices.

The processor 2002 may include, or is in communication with, the memory 2004. The memory 2004 includes computer-readable storage media, that may store instructions that, when executed by the processor 2002, cause the processor 2002 to perform the functions described herein as carried out, or assisted, by the processor 202. Examples of computer-readable media of the memory 2004 may include, but are not limited to a memory chip, ROM, RAM, ASIC, or any other storage means from which a processing device can read or write information. The memory 2004 may store example modules.

The communication link 2006 may be a wireless communication link and may include wireless interfaces, such as IEEE 802.11, BlueTooth™, radio frequency identification (RFID), near-field communication (NFC), or radio interfaces for accessing cellular telephone networks (e.g., transceiver/antenna for accessing a CDMA, GSM, UMTS, or other mobile communications network). In some aspects, the communication link 2006 may be a wired communication link and may include interfaces, such as Ethernet, USB, IEEE 1394, fiber optic interface, voltage signal line, or current signal line. The local control unit 1007 can transmit data to the remote computing device 1009 via the communication link 2006. Likewise the remote computing device 1009 can transmit data to the local control unit 1007 via the communication link 2006. In this manner, the computer system 1005 manages the operation of the sieving apparatus 1000.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

What is claimed is:

1. A male population of mosquito pupae sorted according to a method, wherein the method comprises:
   adding a mixed population of mosquito pupae into an interior volume of a sieving container, the sieving container comprising a base and a perimeter wall encircling the base to form the interior volume, the base defining a set of openings enabling movement of mosquito pupae from the interior volume through the set of openings, and the mixed population of mosquito pupae comprising male mosquito pupae and female mosquito pupae;
   adding a volume of aqueous solution to the interior volume;
   removing a portion of the male mosquito pupae from the mixed population of mosquito pupae to by performing a sieving action that causes the portion of the male mosquito pupae and a portion of the volume of aqueous solution to pass from the interior volume through the set of openings; and capturing the portion of the male mosquito pupae as the male population of mosquito pupae after the portion of the male mosquito pupae has passed through the set of openings.

2. The male population of mosquito pupae of claim 1, wherein individual openings of the set of openings of the sieving container are defined by:
 a length dimension measured along a longitudinal axis of a respective opening; and
 a width dimension measured along a transverse axis of the respective opening, the width dimension corresponding to a representative cephalothorax width of a representative pupae of the mixed population of mosquito pupae.

3. The male population of mosquito pupae of claim 2, wherein the representative cephalothorax width is a narrowest expected cross-sectional cephalothorax width.

4. The male population of mosquito pupae of claim 1, wherein the sieving action comprises moving the sieving container by raising, lowering, agitating, oscillating, and/or shaking the sieving container.

5. The male population of mosquito pupae of claim 1, wherein the male population of mosquito pupae consist of male *Aedes aegypti* mosquito pupae.

6. The male population of mosquito pupae of claim 1, wherein the sieving action causes the mixed population of mosquito pupae to be separated into two groups, a first group consisting of the portion of the male mosquito pupae and a second group comprising female mosquito pupae.

7. A male population of mosquito pupae sorted according to a method, wherein the method comprises:
 adding a volume of aqueous solution comprising a mixed population of mosquito pupae to an interior volume of a sieving container, the sieving container comprising a base and a perimeter wall encircling the base to form the interior volume, the base defining a set of openings enabling movement of mosquito pupae from the interior volume through the set of openings, and the mixed population of mosquito pupae comprising male mosquito pupae and female mosquito pupae;
 performing a sieving action that causes a portion of the male mosquito pupae to be removed from the mixed population according to cephalothorax width, wherein performing the sieving action causes the portion of the male mosquito pupae to pass from the interior volume through the set of openings; and
 capturing the portion of the male pupae as the male population of mosquito pupae after the portion of the male pupae has passed through the set of openings.

8. The male population of mosquito pupae of claim 7, wherein individual openings of the set of openings are defined by:
 a length dimension measured along a longitudinal axis of a respective opening; and
 a width dimension measured along a transverse axis of the respective opening, the width dimension corresponding to a representative cephalothorax width of a representative mosquito pupae of the mixed population of mosquito pupae.

9. The male population of mosquito pupae of claim 8, wherein the representative cephalothorax width is a narrowest expected cross-sectional cephalothorax width.

10. The male population of mosquito pupae of claim 7, wherein performing the sieving action comprises moving the base relative to a first volume of liquid or moving a second volume of liquid relative to the base.

11. The male population of mosquito pupae of claim 7, wherein the base is characterized by a planar surface.

12. The male population of mosquito pupae of claim 11, wherein the set of openings are elongated, and wherein the set of openings are characterized by a repeating pattern of elongated openings extending through the planar surface.

13. The male population of mosquito pupae of claim 7, wherein performing the sieving action separates the mixed population of mosquito pupae into a first set of mosquito pupae that remain within the interior volume and a second set of mosquito pupae that pass through the set of openings, wherein the male population of mosquito pupae comprises the second set of the mosquito pupae.

14. The male population of mosquito pupae of claim 13, wherein the first set of mosquito pupae are substantially female mosquito pupae and the second set of mosquito pupae are substantially male mosquito pupae.

15. A population of male *Aedes aegypti* mosquito pupae sorted according to a method, wherein the method comprises:
 pouring a mixed population of mosquito pupae onto a base of a sieving container defining an interior volume, the base defining a set of openings enabling movement of mosquito pupae from the interior volume through the set of openings, the set of openings sized according to a cephalothorax width of a representative mosquito pupae from the mixed population of mosquito pupae, and the mixed population of mosquito pupae comprising male *Aedes aegypti* mosquito pupae and female *Aedes aegypti* mosquito pupae;
 removing a portion of the male *Aedes aegypti* pupae from the mixed population of mosquito pupae by introducing a volume of aqueous solution onto the base of the sieving container, wherein the volume of aqueous solution causes the portion of the male *Aedes aegypti* mosquito pupae to pass from the interior volume through the set of openings; and
 capturing the portion of the male *Aedes aegypti* pupae as the population of male *Aedes aegypti* mosquito pupae after the portion of the male *Aedes aegypti* pupae has passed through the set of openings.

16. The population of male *Aedes aegypti* mosquito pupae of claim 15, wherein individual openings of the set of openings are defined by:
 a length dimension measured along a longitudinal axis of a respective opening; and
 a width dimension measured along a transverse axis of the respective opening, the width dimension corresponding to a representative cephalothorax width of a representative *Aedes aegypti* pupae of the mixed population of mosquito pupae.

17. The population of male *Aedes aegypti* mosquito pupae of claim 16, wherein the representative cephalothorax width is a narrowest expected cross-sectional cephalothorax width.

18. The population of male *Aedes aegypti* mosquito pupae of claim 15, wherein the base is characterized by a planar surface.

19. The population of male *Aedes aegypti* mosquito pupae of claim 18, wherein the set of openings are elongated, and wherein the set of openings are characterized by a repeating pattern of elongated openings extending through the planar surface.

20. The population of male *Aedes aegypti* mosquito pupae of claim 15, wherein the method further comprises performing a sieving action by moving the sieving container by raising, lowering, agitating, oscillating, and/or shaking the sieving container.

\* \* \* \* \*